United States Patent
Zheng et al.

(10) Patent No.: US 12,156,989 B2
(45) Date of Patent: Dec. 3, 2024

(54) SYSTEMS, APPARATUSES AND METHODS FOR OCCLUSION DETECTION USING PUMP OPERATION MEASUREMENT

(71) Applicant: Becton, Dickinson and Company, Franklin Lakes, NJ (US)

(72) Inventors: Ling Zheng, Acton, MA (US); Mojtaba Kashef, Boxford, MA (US); Uzair Siddiqui, Jersey City, NJ (US); Jinyan Li, Chelmsford, MA (US); Kepei Sun, Andover, MA (US); Joseph Iskandar, Roslindale, MA (US); Elizabeth Gurin, Franklin Lakes, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 562 days.

(21) Appl. No.: 16/967,330

(22) PCT Filed: Jan. 29, 2019

(86) PCT No.: PCT/US2019/015622
§ 371 (c)(1),
(2) Date: Aug. 4, 2020

(87) PCT Pub. No.: WO2019/156852
PCT Pub. Date: Aug. 15, 2019

(65) Prior Publication Data
US 2021/0030953 A1    Feb. 4, 2021

Related U.S. Application Data
(60) Provisional application No. 62/764,998, filed on Aug. 20, 2018, provisional application No. 62/663,682, (Continued)

(51) Int. Cl.
*A61M 5/168*    (2006.01)
*A61M 5/142*    (2006.01)

(52) U.S. Cl.
CPC .... *A61M 5/16831* (2013.01); *A61M 5/14212* (2013.01); *A61M 2005/14208* (2013.01);
(Continued)

(58) Field of Classification Search
CPC .......... A61M 5/16831; A61M 5/14212; A61M 2005/14208; A61M 2005/16863;
(Continued)

(56) References Cited

U.S. PATENT DOCUMENTS

| | | | |
|---|---|---|---|
| 4,373,525 A | 2/1983 | Kobayashi | |
| 4,950,235 A * | 8/1990 | Slate ..................... | A61M 5/365 128/DIG. 13 |

(Continued)

FOREIGN PATENT DOCUMENTS

| | | |
|---|---|---|
| JP | H01300962 A | 12/1989 |
| JP | 2007-530860 A | 11/2007 |

(Continued)

OTHER PUBLICATIONS

International Search Report dated Apr. 26, 2019, which issued in the corresponding PCT Patent Application No. PCT/US2019/015622.

*Primary Examiner* — Kami A Bosworth
*Assistant Examiner* — Avery Smale
(74) *Attorney, Agent, or Firm* — Dickinson Wright PLLC

(57) ABSTRACT

A technical solution for monitoring operation of a medical delivery device such as an infusion pump for occlusion is provided that employs sensing pump motor current and monitoring average motor current difference as between dispense and aspirate strokes in a pump cycle. The solution can be implemented alone or in combination with other occlusion sensing methods that use one or more of pump
(Continued)

measurement data such as pump stroke duration (e.g., duration of aspirate stroke or dispense stroke in a rotational metering-type pump or a reciprocating-type pump), end-stop or limit switch activation, and duration difference between aspirate and dispense strokes to detect occlusion.

22 Claims, 34 Drawing Sheets

Related U.S. Application Data filed on Apr. 27, 2018, provisional application No. 62/626,909, filed on Feb. 6, 2018.

(52) U.S. Cl.
CPC ............. *A61M 2005/16863* (2013.01); *A61M 2205/18* (2013.01); *A61M 2205/3331* (2013.01)

(58) Field of Classification Search
CPC ...... A61M 2205/18; A61M 2205/3331; A61M 2005/16868; A61M 2005/16872; A61M 2205/3306; A61M 2205/3317; A61M 2205/3375; A61M 2205/3327
See application file for complete search history.

(56) References Cited

U.S. PATENT DOCUMENTS

| | | |
|---|---|---|
| 5,131,816 A | 7/1992 | Brown et al. |
| 5,328,460 A | 7/1994 | Lord et al. |
| 5,647,853 A | 7/1997 | Feldmann et al. |
| 5,803,712 A | 9/1998 | Davis et al. |
| 6,423,035 B1 | 7/2002 | Das et al. |
| 6,485,465 B2 | 11/2002 | Moberg et al. |
| 6,555,986 B2 | 4/2003 | Moberg |
| 6,656,148 B2 | 12/2003 | Das et al. |
| 6,659,980 B2 | 12/2003 | Moberg et al. |
| 6,923,782 B2 | 8/2005 | O'Mahony et al. |
| 7,193,521 B2 | 3/2007 | Moberg et al. |
| 7,621,893 B2 | 11/2009 | Moberg et al. |
| 7,766,873 B2 | 8/2010 | Moberg et al. |
| 7,828,528 B2 | 11/2010 | Estes et al. |
| 7,892,206 B2 | 2/2011 | Moberg et al. |
| 7,998,111 B2 | 8/2011 | Moberg et al. |
| 8,065,096 B2 | 11/2011 | Moberg et al. |
| 8,182,447 B2 | 5/2012 | Moberg et al. |
| 8,378,837 B2 | 2/2013 | Wang et al. |
| 8,469,942 B2 | 6/2013 | Kow et al. |
| 8,483,980 B2 | 7/2013 | Moberg et al. |
| 8,647,296 B2 | 2/2014 | Moberg et al. |
| 8,668,672 B2 | 3/2014 | Moberg et al. |
| 8,681,010 B2 | 3/2014 | Moberg et al. |
| 8,715,237 B2 | 5/2014 | Moberg et al. |
| 8,790,294 B2 | 7/2014 | Estes |
| 8,864,739 B2 | 10/2014 | Moberg et al. |
| 8,900,213 B2 | 12/2014 | Pope et al. |
| 9,011,371 B2 | 4/2015 | Moberg et al. |
| 9,033,925 B2 | 5/2015 | Moberg et al. |
| 9,050,406 B2 | 6/2015 | Kow et al. |
| 9,107,999 B2 | 8/2015 | Moberg et al. |
| 9,119,910 B2 | 9/2015 | Wiegel |
| 9,327,073 B2 | 5/2016 | Moberg et al. |
| 9,364,608 B2 | 6/2016 | Moberg et al. |
| 9,433,732 B2 | 9/2016 | Moberg et al. |
| 9,433,733 B2 | 9/2016 | Moberg et al. |
| 9,610,404 B2 | 4/2017 | Rotstein |
| 9,717,849 B2 | 8/2017 | Mhatre et al. |
| 9,731,072 B2 | 8/2017 | Estes |
| 9,879,668 B2 | 1/2018 | Yavorsky et al. |
| 9,895,490 B2 | 2/2018 | Kow et al. |
| 9,962,486 B2 | 5/2018 | Rosinko et al. |
| 9,987,425 B2 | 6/2018 | Alderete et al. |
| 9,993,594 B2 | 6/2018 | Bazargan et al. |
| 10,010,668 B2 | 7/2018 | Tieck |
| 10,219,985 B2 | 3/2019 | Hudson |
| 10,226,573 B2 | 3/2019 | Baek et al. |
| 2004/0133166 A1 | 7/2004 | Moberg et al. |
| 2005/0238503 A1* | 10/2005 | Rush ................. F03G 7/065 417/322 |
| 2007/0112301 A1* | 5/2007 | Preuthun ............. F04B 43/04 604/151 |
| 2008/0175719 A1 | 7/2008 | Tracey et al. |
| 2008/0221523 A1* | 9/2008 | Moberg ............ A61M 5/16854 604/151 |
| 2011/0060284 A1 | 3/2011 | Harr |
| 2014/0058351 A1 | 2/2014 | Pope et al. |
| 2015/0182697 A1 | 7/2015 | Panzer |
| 2016/0303318 A1* | 10/2016 | Burke ............... A61M 5/14593 |
| 2016/0367750 A1* | 12/2016 | Tieck ................ A61M 5/14216 |
| 2016/0367751 A1 | 12/2016 | Bazargan |
| 2017/0203036 A1 | 7/2017 | Mazlish et al. |
| 2019/0142699 A1 | 5/2019 | Hudson |
| 2019/0143034 A1 | 5/2019 | Anderson et al. |
| 2020/0070517 A1 | 3/2020 | Sato et al. |

FOREIGN PATENT DOCUMENTS

| | | |
|---|---|---|
| JP | 2014-057886 A | 4/2014 |
| JP | 2017-35647 A | 2/2017 |
| WO | 2005094919 A1 | 10/2005 |

* cited by examiner

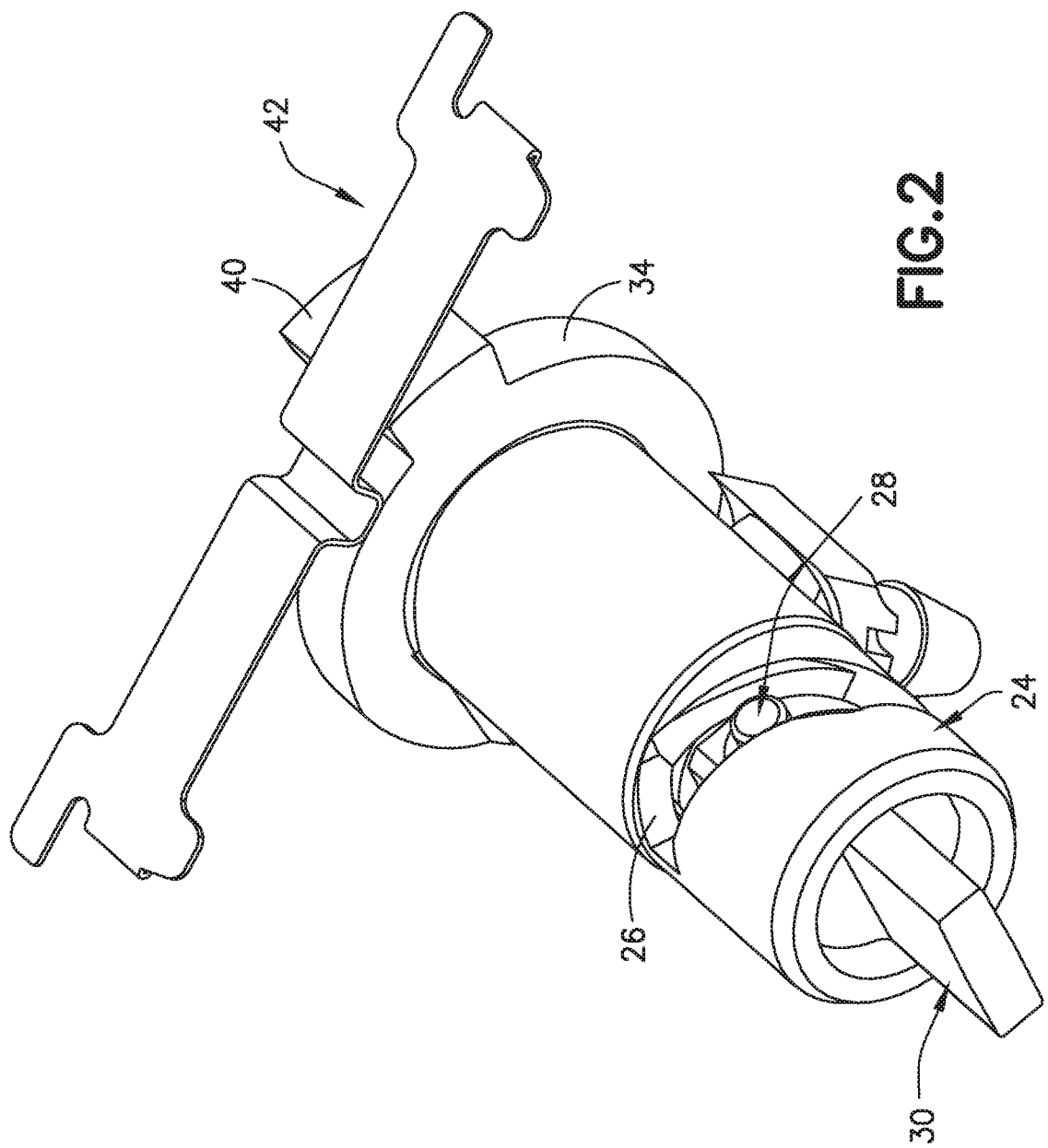

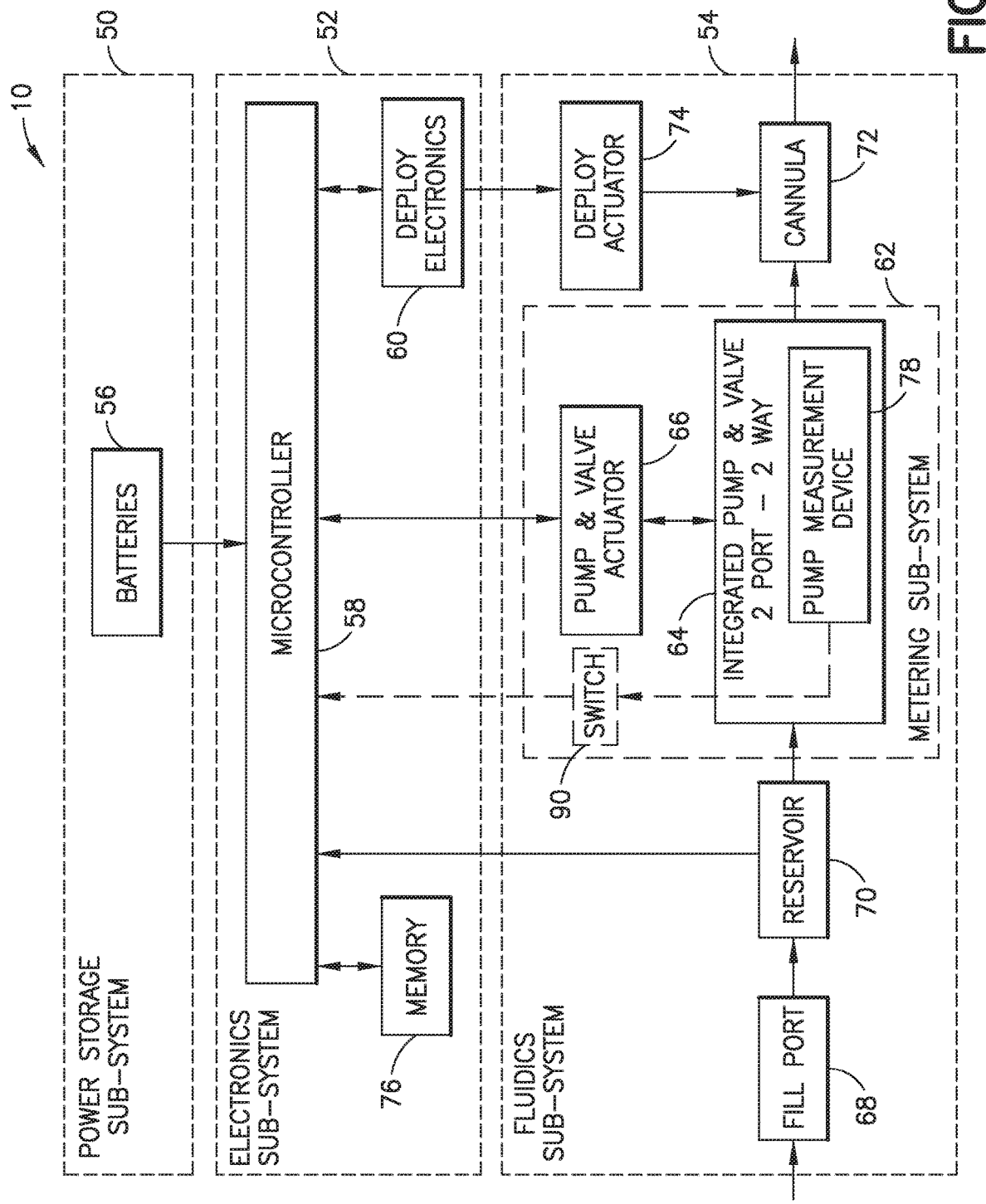

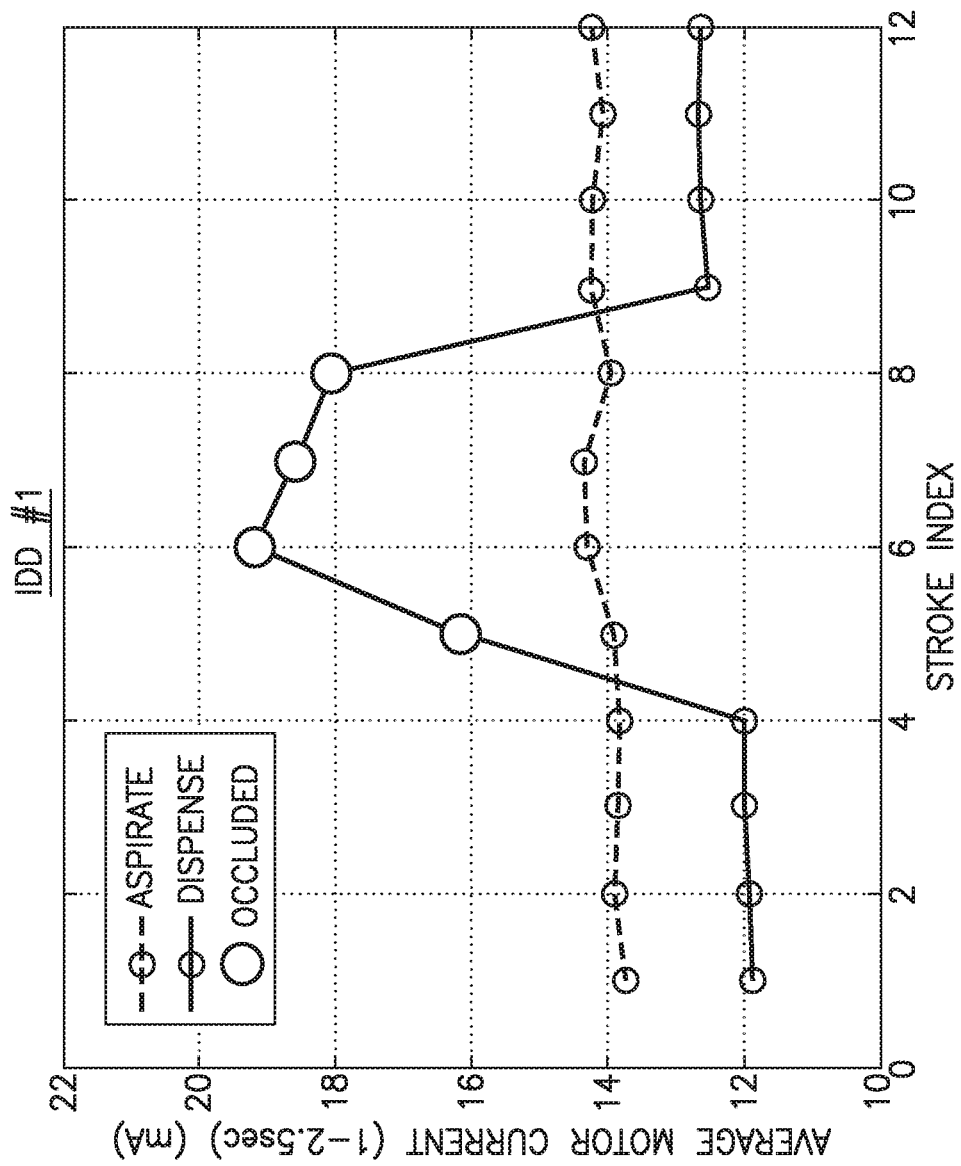

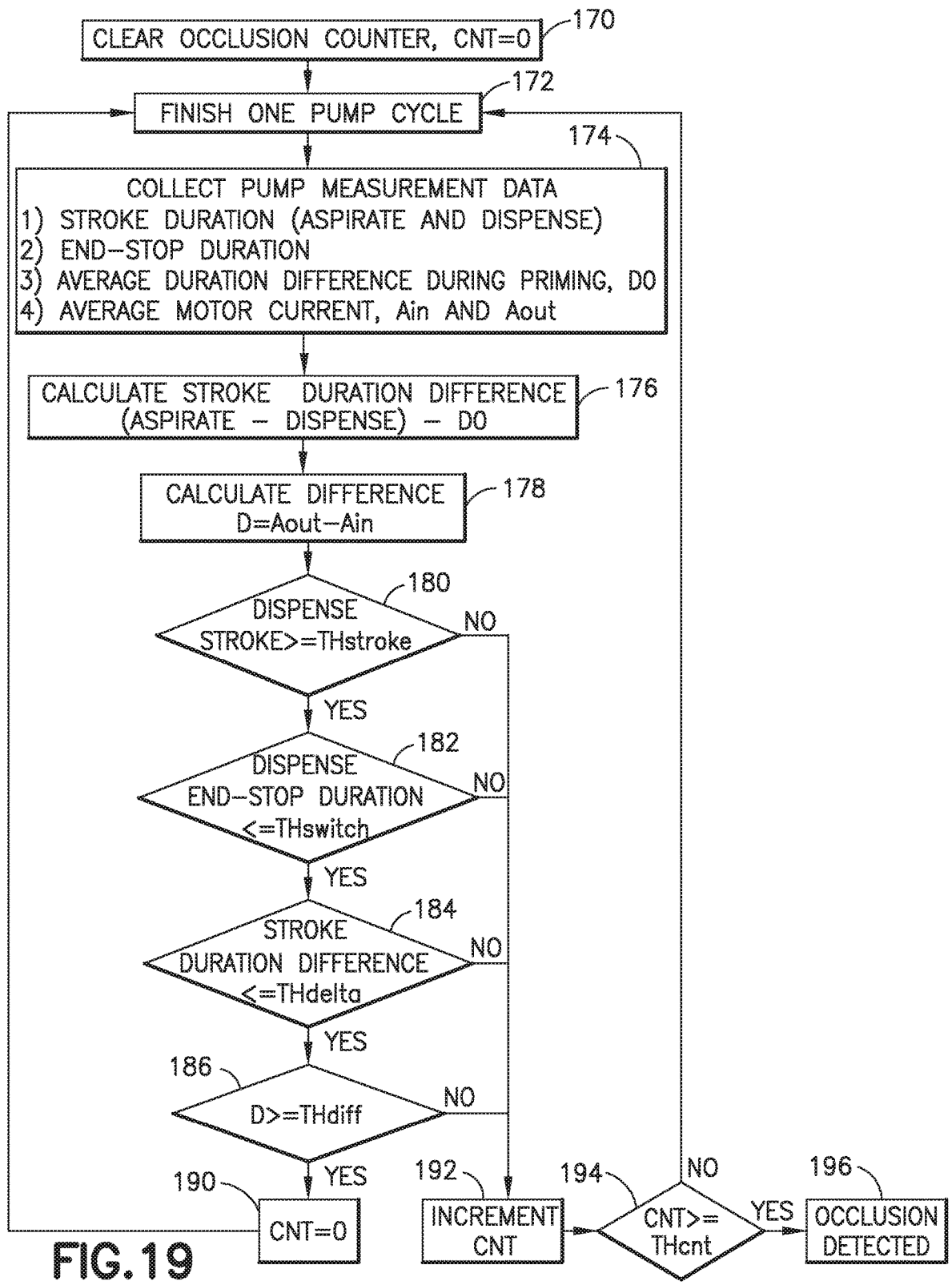

SYSTEMS, APPARATUSES AND METHODS FOR OCCLUSION DETECTION USING PUMP OPERATION MEASUREMENT

This application is a 35 U.S.C. § 371 national stage patent application based on PCT Application No. PCT/US2019/015622, filed Jan. 29, 2019, which claims the benefit of U.S. Provisional Application Ser. No. 62/764,998, filed Aug. 20, 2018, which claims the benefit of U.S. Provisional Application Ser. No. 62/663,682, filed Apr. 27, 2018, which claims the benefit of U.S. Provisional Application Ser. No. 62/626,909, filed Feb. 6, 2018, the entire contents of each of which are incorporated herein by reference.

BACKGROUND

Field

The present invention relates to systems, methods and apparatuses for occlusion detection. Illustrative embodiments of the present invention relate to occlusion detection using a pump operation parameter such as pump duration (e.g., aspirate or dispense stroke duration) in a rotational metering or reciprocating pump, or pump operation monitoring switch activation, to obviate adding an additional pressure sensing component. Pump motor current sensing can also be employed to detect occlusion conditions in a pump.

Description of Related Art

Diabetes is a group of diseases characterized by high levels of blood glucose resulting from the inability of diabetic patients to maintain proper levels of insulin production when required. Diabetes can be dangerous to the affected patient if it is not treated, and it can lead to serious health complications and premature death. However, such complications can be minimized by utilizing one or more treatment options to help control the diabetes and reduce the risk of complications.

The treatment options for diabetic patients include specialized diets, oral medications and/or insulin therapy. An effective method for insulin therapy and managing diabetes is infusion therapy or infusion pump therapy in which an insulin pump is used. The insulin pump can provide continuous infusion of insulin to a diabetic patient at varying rates in order to more closely match the functions and behavior of a properly operating pancreas of a non-diabetic person that produces the required insulin, and the insulin pump can help the diabetic patient maintain his/her blood glucose level within target ranges based on the diabetic patient's individual needs. Infusion pump therapy requires an infusion cannula, typically in the form of an infusion needle or a flexible catheter, that pierces the diabetic patient's skin and through which infusion of insulin takes place. Infusion pump therapy offers the advantages of continuous infusion of insulin, precision dosing, and programmable delivery schedules.

Anomalies or dysfunctions such as leaks, occlusions or presence of air bubbles in a fluid path can occur in an infusion pump and are not necessarily noticeable to the user. Detection of a dysfunction such as a partial or total occlusion along a fluid path in an infusion pump can be desirable to maintain accurately controlled medication delivery and to advise the user to discontinue use of a malfunctioning infusion device. A typical solution for occlusion detection is to place a pressure sensor in the infusion pump system and report occlusion when the pressure is above a certain threshold. Adding a pressure sensor, however, increases the complexity of the system (e.g., increases mechanical, electrical, and/or software complexity), increases system power consumption, and increases the cost of the infusion pump.

For medical devices such as a wearable medication delivery pump, where some or all of the components are disposable for ease of use and cost effectiveness, adding another component such as a pressure sensor and related increased cost and complexity to the medical device is undesirable. A need therefore exists for accurate occlusion detection without adding infusion pump components and thereby increasing infusion pump complexity and cost.

SUMMARY

The above and other problems are overcome, and additional advantages are realized, by illustrative embodiments of the present invention.

It is an aspect of illustrative embodiments to provide an infusion device with integral occlusion sensing comprising: a pump comprising a chamber configured with at least one port to receive fluid into the chamber from a reservoir and through which fluid flows out of the chamber, and a pumping mechanism configured to control aspiration of a volume of the fluid into the chamber during an aspirate stroke and to control dispensing of a volume of fluid from the chamber during a dispense stroke; a pump measurement device configured to generate pump measurement related to at least one of each aspirate stroke performed by the pump and each dispense stroke performed by the pump; and a processing device configured to analyze pump measurements comprising the pump measurement for each of a plurality of the at least one of the aspirate stroke and the dispense stroke and determine when the pump measurements comprise a plurality of the pump measurement that satisfy a predetermined metric designated as an indication of occlusion.

In accordance with aspects of illustrative embodiments of the present invention, the infusion pump with integral occlusion sensing further comprises an indicator, and the processing device is configured to operate the indicator as an occlusion alert in response to a determination that a plurality of the pump measurement satisfy the predetermined metric.

In accordance with aspects of illustrative embodiments of the present invention, the processing device is configured to automatically terminate operation of the pumping mechanism in response to a determination that a plurality of the pump measurement satisfy the predetermined metric.

In accordance with aspects of illustrative embodiments of the present invention, the pump measurement corresponds to a time duration of the at least one of the aspirate stroke and the dispense stroke, and the predetermined metric is a selected time duration that is shorter than an average value of the pump measurement when no occlusion is occurring in the pump.

In accordance with aspects of illustrative embodiments of the present invention, the pump measurement device is an end-stop switch on the pump configured to be activated when the pumping mechanism completes the at least one of the aspirate stroke and the dispense stroke. The end-stop switch is connected to the processing device to determine time duration of each of the at least one of the aspirate stroke and the dispense stroke.

In accordance with aspects of illustrative embodiments of the present invention, the pump measurement corresponds to a duration of end-stop switch activation, and the predetermined metric is a selected time duration for end-stop switch activation that is longer than an average value of the pump measurement when no occlusion is occurring in the pump.

In accordance with aspects of illustrative embodiments of the present invention, the infusion device with integral occlusion sensing further comprises a current sensing device configured to detect pumping mechanism current during at least one of the aspirate stroke and the dispense stroke of a pump cycle for a plurality of such pump cycle. The pump measurement corresponds to the pumping mechanism current; and the pump measurements comprise the pumping mechanism current for a selected number of the plurality of pump cycles. The predetermined metric comprises an average pumping mechanism current that exceeds a designated current value that is higher than an average value of the pumping mechanism current when no occlusion is occurring in the pump. For example, the processing device can be configured to determine, for each of a plurality of pump cycles, an average pumping mechanism current of the aspirate stroke, and average pumping mechanism current of the dispense stroke, and a difference between the average pumping mechanism current of the dispense stroke and the average pumping mechanism current of the aspirate stroke. The predetermined metric can be a designated value for the difference that, when exceeded, indicates occlusion.

In accordance with aspects of illustrative embodiments of the present invention, the pump measurement device is an end-stop switch on the pump configured to be activated when the pumping mechanism completes the at least one of the aspirate stroke and the dispense stroke. The end-stop switch is connected to the processing device to determine time duration of each of the at least one of the aspirate stroke and the dispense stroke, such that, for a pump measurement that corresponds to a duration of end-stop switch activation, the predetermined metric is a selected time duration for end-stop switch activation that is longer than an average value of the pump measurement when no occlusion is occurring in the pump. The pump measurement comprises at least two of the end-stop switch activation duration, a duration of the at least one of the aspirate stroke and the dispense stroke, a time difference between the aspirate stroke and the dispense stroke, and the difference between the average pumping mechanism current of the dispense stroke and the average pumping mechanism current of the aspirate stroke. The predetermined metric corresponding to stroke duration is a selected time duration that is shorter than an average value of the stroke duration when no occlusion is occurring in the pump. The predetermined metric corresponding to a dispense stroke duration difference relative to an aspirate stroke duration is a selected time duration that is greater than an average value of the stroke duration difference when no occlusion is occurring in the pump. The processing device is configured to analyze the pump measurements comprising and determine when the pump measurements comprise a plurality of the pump measurement that satisfy a corresponding one of the predetermined metric.

In accordance with aspects of illustrative embodiments of the present invention, the pump measurement corresponds to a time difference between the aspirate stroke and the dispense stroke, and the predetermined metric corresponding to a dispense stroke duration difference relative to an aspirate stroke duration is a selected time duration that is greater than an average value of the stroke duration difference when no occlusion is occurring in the pump. In accordance with aspects of illustrative embodiments of the present invention, the pump measurement can also comprise time duration of the at least one of the aspirate stroke and the dispense stroke, and the predetermined metric corresponding to the stroke duration is a selected time duration that is shorter than an average value of the stroke duration when no occlusion is occurring in the pump. The processing device is configured to and analyze the pump measurements and determine when the pump measurements comprise a plurality of the pump measurement that satisfy a corresponding one of the predetermined metric.

It is an aspect of illustrative embodiments of the present invention to provide a method of occlusion sensing in an infusion pump comprising: operating a pump comprising a chamber configured with at least one port to receive fluid into the chamber from a reservoir and through which fluid flows out of the chamber, and a pumping mechanism configured to control aspiration of a volume of the fluid into the chamber during an aspirate stroke and to control dispensing of a volume of fluid from the chamber during a dispense stroke; operating a pump measurement device to generate a pump measurement related to at least one of each aspirate stroke performed by the pump and each dispense stroke performed by the pump; and analyzing pump measurements comprising the pump measurement for each of a plurality of the at least one of the aspirate stroke and the dispense stroke to determine when the pump measurements comprise a plurality of the pump measurement that satisfy a predetermined metric designated as an indication of occlusion.

In accordance with aspects of illustrative embodiments of the present invention, the method of occlusion sensing further comprises activating an indicator an occlusion alert in response to a determination that a plurality of the pump measurement satisfy the predetermined metric.

In accordance with aspects of illustrative embodiments of the present invention, the method of occlusion sensing further comprises automatically terminating operation of the pumping mechanism in response to a determination that a plurality of the pump measurement satisfy the predetermined metric.

In accordance with aspects of illustrative embodiments of the present invention, the method of occlusion sensing further comprises operating the pump measurement device to generate a pump measurement that corresponds to a time duration of the at least one of the aspirate stroke and the dispense stroke. For example, the method of occlusion sensing can use the predetermined metric as a selected time duration that is shorter than an average value of the pump measurement when no occlusion is occurring in the pump.

In accordance with aspects of illustrative embodiments of the present invention, the method of occlusion sensing further comprises configuring the pump measurement device as an end-stop switch on the pump that is activated when the pumping mechanism completes the at least one of the aspirate stroke and the dispense stroke; and connecting the end-stop switch to a processing device configured to analyze signals from the end-stop switch to determine time duration of each of the at least one of the aspirate stroke and the dispense stroke.

In accordance with aspects of illustrative embodiments of the present invention, the pump measurement corresponds to a duration of end-stop switch activation, and the predetermined metric is a selected time duration for end-stop switch activation that is longer than an average value of the pump measurement when no occlusion is occurring in the pump.

In accordance with aspects of illustrative embodiments of the present invention, a method of occlusion sensing comprises detecting pumping mechanism current during at least one of the aspirate stroke and the dispense stroke of a pump cycle for a plurality of such pump cycle. The pump measurement corresponds to the pumping mechanism current.

The pump measurements comprise the pumping mechanism current for a selected number of the plurality of pump cycles. The predetermined metric comprises an average pumping mechanism current that exceeds a designated current value that is higher than an average value of the pumping mechanism current when no occlusion is occurring in the pump. For example, analyzing pump measurements can comprises determining, for each of a plurality of pump cycles, an average pumping mechanism current of the aspirate stroke, and average pumping mechanism current of the dispense stroke, and a difference between the average pumping mechanism current of the dispense stroke and the average pumping mechanism current of the aspirate stroke. The predetermined metric is a designated value for the difference that, when exceeded, indicates occlusion.

In accordance with aspects of illustrative embodiments of the present invention, the method of occlusion sensing further comprises configuring the pump measurement device as an end-stop switch on the pump that is activated when the pumping mechanism completes the at least one of the aspirate stroke and the dispense stroke such that, for a pump measurement that corresponds to a duration of end-stop switch activation, the predetermined metric is a selected time duration for end-stop switch activation that is longer than an average value of the pump measurement when no occlusion is occurring in the pump. The pump measurement comprises at least two of the end-stop switch activation duration, a duration of the at least one of the aspirate stroke and the dispense stroke, a time difference between the aspirate stroke and the dispense stroke, and the difference between the average pumping mechanism current of the dispense stroke and the average pumping mechanism current of the aspirate stroke. The predetermined metric corresponding to stroke duration is a selected time duration that is shorter than an average value of the stroke duration when no occlusion is occurring in the pump, and the predetermined metric corresponding to a dispense stroke duration difference relative to an aspirate stroke duration is a selected time duration that is greater than an average value of the stroke duration difference when no occlusion is occurring in the pump. Analyzing the pump measurements comprises determining when the pump measurements comprise a plurality of the pump measurement that satisfy a corresponding one of the predetermined metric.

In accordance with aspects of illustrative embodiments of the present invention, the pump measurement corresponds to a time difference between the aspirate stroke and the dispense stroke, and the predetermined metric corresponding to a dispense stroke duration difference relative to an aspirate stroke duration is a selected time duration that is greater than an average value of the stroke duration difference when no occlusion is occurring in the pump. The pump measurement can also comprise time duration of the at least one of the aspirate stroke and the dispense stroke, and the predetermined metric corresponding to the stroke duration is a selected time duration that is shorter than an average value of the stroke duration when no occlusion is occurring in the pump. Analyzing the pump measurements comprises determining when the pump measurements comprise a plurality of the pump measurement that satisfy a corresponding one of the predetermined metric.

Additional and/or other aspects and advantages of embodiments of the present invention will be set forth in the description that follows, or will be apparent from the description, or may be learned by practice of the invention. The present invention may comprise devices and methods for operating same having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The above and/or other aspects and advantages of embodiments of the invention will be more readily appreciated from the following detailed description, taken in conjunction with the accompanying drawings, of which:

FIGS. 1 and 2 are partial, perspective views of example pump components in an example medication delivery device that operates in accordance with an occlusion detection algorithm in accordance with an illustrative embodiment of the present invention;

FIG. 4 is a block diagram of components in an example medication delivery device;

FIGS. 18A, 18B, 18C, 18D and 18E depict average motor current for a selected time period for respective example delivery devices; and FIG. 19 is a flow chart of illustrative operations of an example medication delivery device that operates in accordance with an occlusion detection algorithm employing a combination of criteria with pump motor current criteria in accordance with an illustrative embodiment of the present invention.

Throughout the drawing figures, like reference numbers will be understood to refer to like elements, features and structures.

DETAILED DESCRIPTION OF ILLUSTRATIVE EMBODIMENTS

Figure 1:
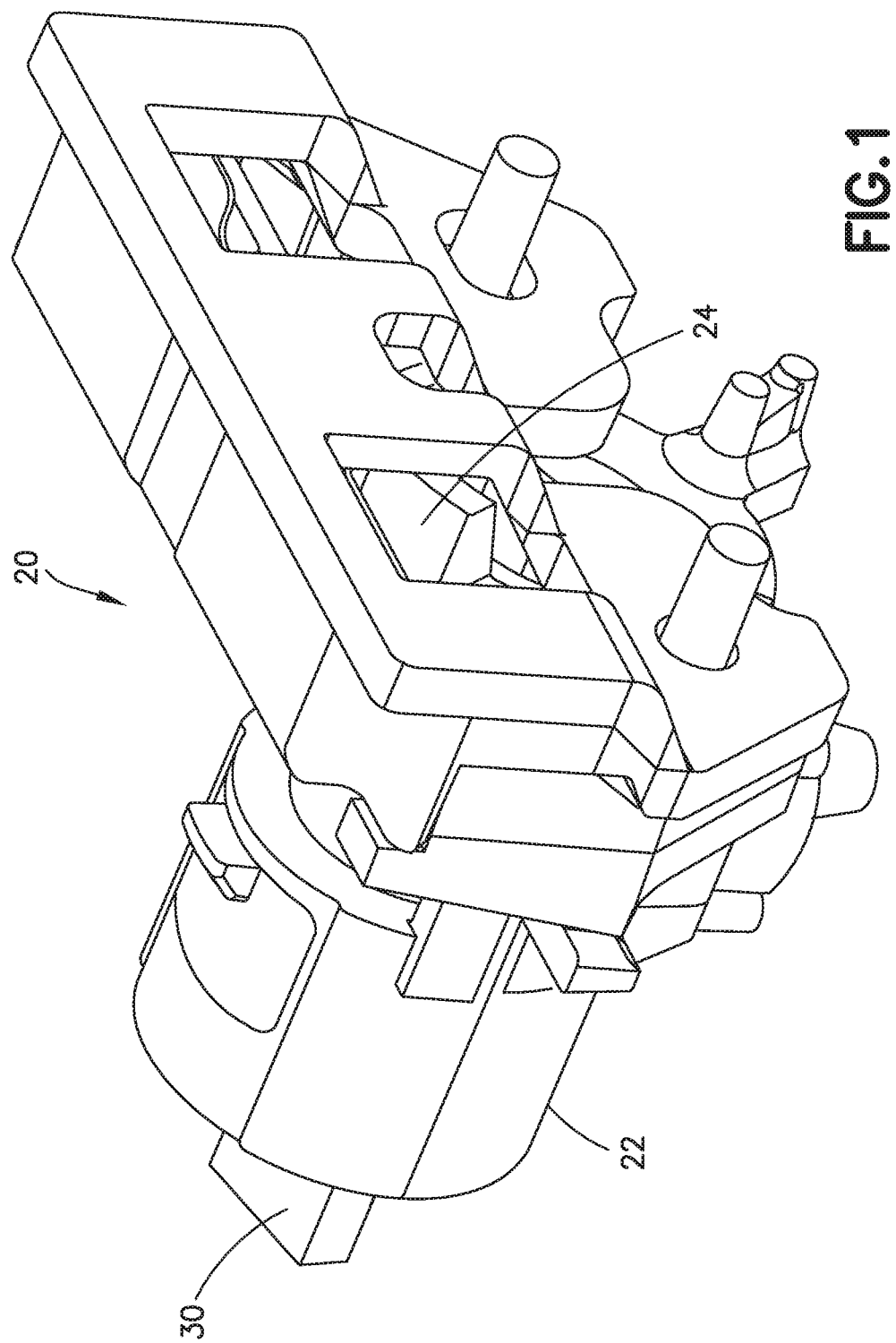

Reference will now be made in detail to example embodiments of the present invention, which are illustrated in the accompanying drawings. The example embodiments described herein exemplify, but do not limit, the present invention by referring to the drawings.

Illustrative embodiments can be employed with any type of infusion pump that works on the principle of filling a chamber (e.g., with liquid medication from a reservoir) in one stage and then emptying the fluid from the chamber (e.g., to a delivery device such as a cannula deployed in a patient) in another stage. For example, a reciprocating plunger-type pump or a rotational metering-type pump can be used. In either case, a piston or plunger is retracted from a chamber to aspirate or draw medication into the chamber and allow the chamber to fill with a volume of medication (e.g., from a reservoir or cartridge of medication into an inlet port). The piston or plunger is then re-inserted into the chamber to dispense or discharge a volume of the medication from the chamber (e.g., via an outlet port) to a fluid pathway extending between the pump and a cannula in the patient.

Figure 3A:
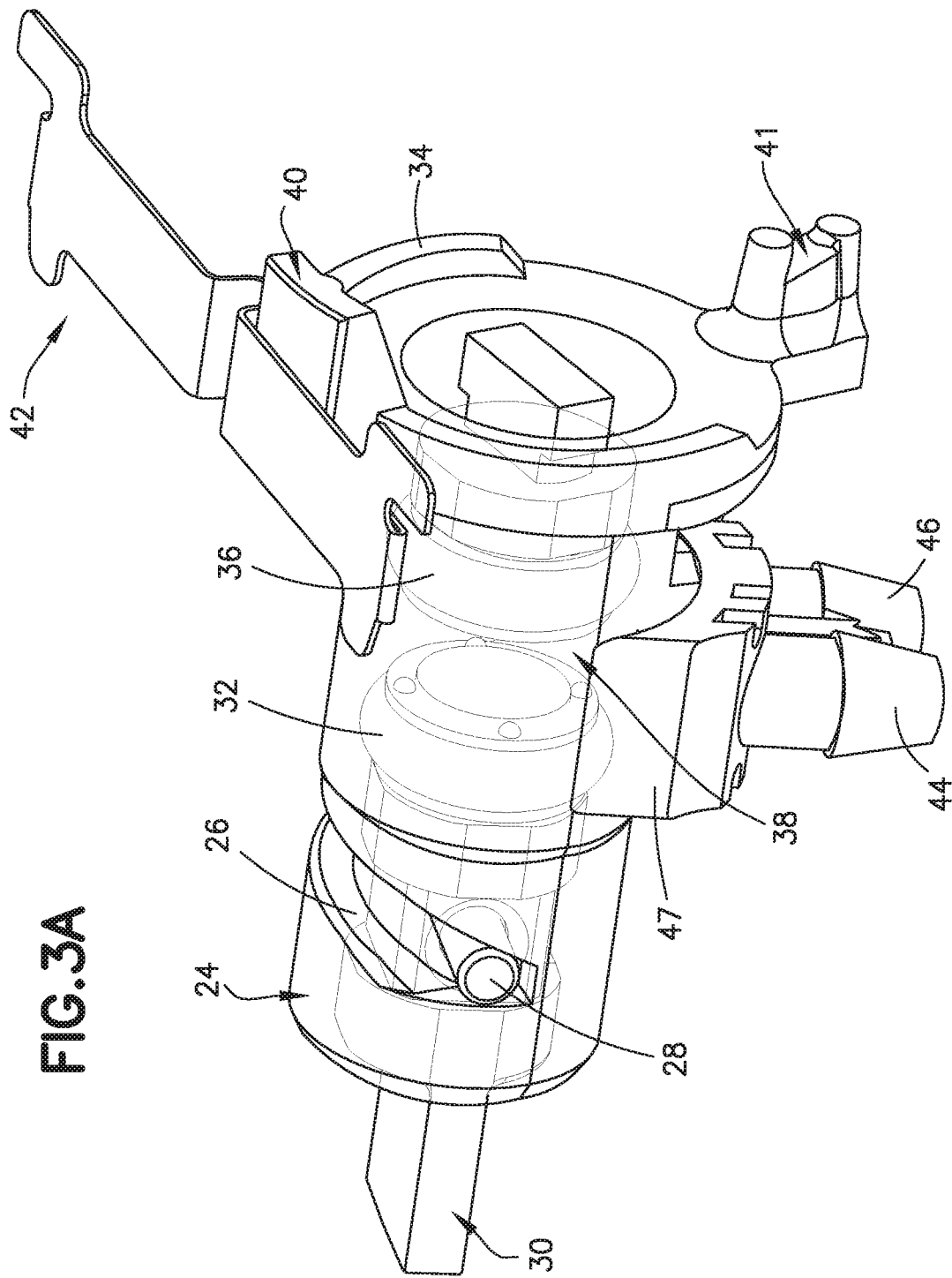
FIGS. 3A and 3B are perspective views of pump components of FIGS. 1 and 2 in an example medication delivery device arranged, respectively, in accordance with a ready to dispense stage of operation and a ready to aspirate stage of operation.
Figure 3B:
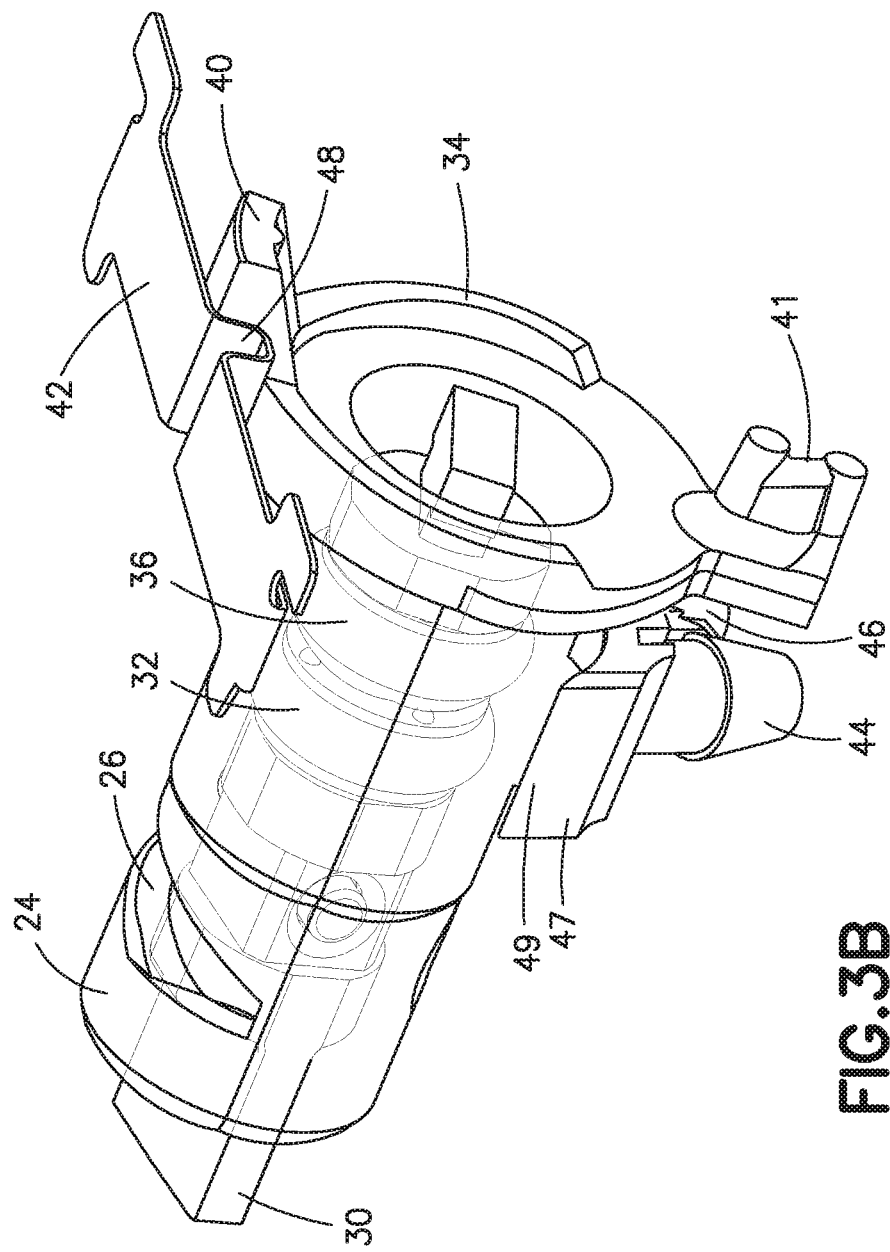

For illustrative purposes, reference is made to an example rotational metering-type pump described in commonly owned WO 2015/157174, the content of which is incorporated herein by reference in its entirety. With reference to FIGS. 1, 2, 3A, 3B and 3C, an example infusion pump (e.g., a wearable medication delivery device such as an insulin patch pump) comprises a pump assembly 20 which can be connected to a DC motor and gearbox assembly (not shown) to rotate a sleeve 24 in a pump manifold 22. A helical groove 26 is provided on the sleeve. A coupling pin 28 connected to a piston 30 translates along the helical groove to guide the retraction and insertion of the piston 30 within the sleeve 24, respectively, as the sleeve 24 rotates in one direction and then rotates in the opposite direction. The sleeve has an end plug 34. Two seals 32, 36 on the respective ends of the piston and end plug that are interior to the sleeve 24 define a cavity or chamber 38 when the piston 30 is retracted, as depicted in FIG. 3A, following an aspirate stroke and therefore ready to dispense. The volume of the chamber 38 therefore changes depending on the degree of retraction of the piston 30. The volume of the chamber 38 is negligible or essentially zero when the piston 30 is fully inserted and the seals 32, 36 are substantially in contact with each other following a dispense stroke, as depicted in FIG. 3B, and therefore ready to aspirate. Two ports 44, 46 are provided relative to the pump manifold 22, including an inlet port 44 through which medication can flow from a reservoir 70 (FIG. 4) for the pump 64 (FIG. 4), and an outlet port 46 through which the medication that has been drawn into the chamber 38 (e.g., by retraction of the piston 30 during an aspirate stage of operation) can be dispensed from the chamber 38 to, for example, a fluid path to a cannula 72 (FIG. 4) in the patient by re-insertion of the piston 30 into the chamber 38.

Figure 3C:
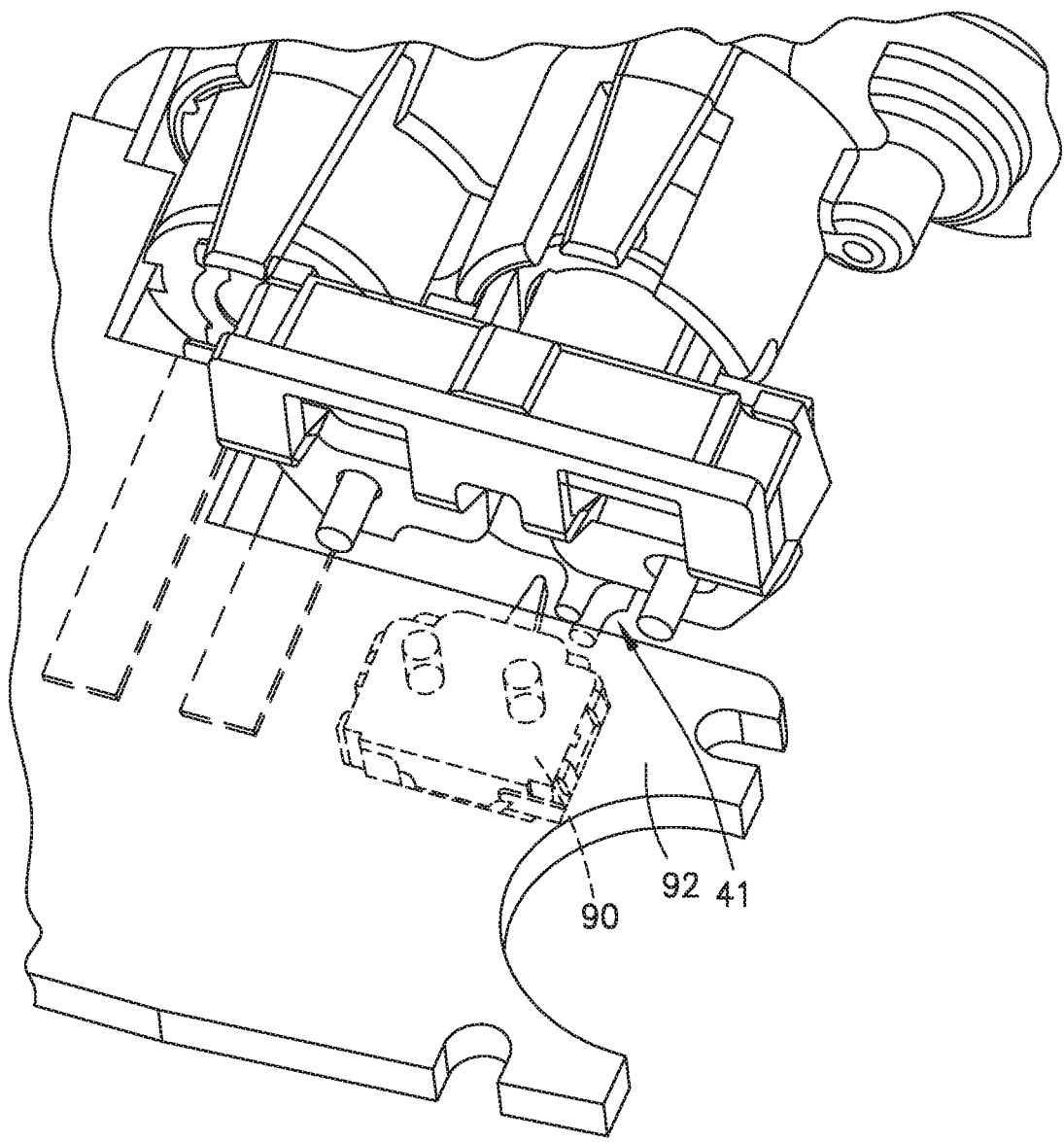
FIG. 3C is a perspective view of components in an example medication delivery device comprising example pump components of FIGS. 1 and 2 and associated electronic circuits on a printed circuit board.

With continued reference to FIGS. 1, 2, 3A, 3B and 3C, the sleeve 24 can be provided with an aperture (not shown) that aligns with the outlet port 46 or the inlet port 44 (i.e., depending on the degree of rotation of the sleeve 24 and therefore the degree of translation of the piston 30) to permit the medication in the chamber 38 to flow through the corresponding one of the ports 44, 46. A pump measurement device 78 (FIG. 4) such as a sleeve rotational limit switch can be provided which has, for example, an interlock 42 and one or more detents 40 on the sleeve 24 or its end ping 34 that cooperate with the interlock 42. The interlock 42 can be mounted to the manifold 22 at each end thereof. The detent 40 at the end face of sleeve 24 is adjacent to a bump 48 of the interlock 42 when the pump 64 is in a first position whereby a side hole in the sleeve 24 is aligned with the inlet port 44 to receive fluid from the reservoir 70 into the chamber 38. Under certain conditions, such as back pressure, it is possible that friction between the piston 30 and the sleeve 24 is sufficient to cause the sleeve 24 to rotate before the piston 30 and coupling pin 28 reach either end of the helical groove 26. This could result in an incomplete volume of liquid being pumped per stroke. In order to prevent this situation, the interlock 42 prevents the sleeve 24 from rotating until the torque passes a predetermined threshold, as shown in FIG. 3A. This ensures that piston 30 fully rotates within the sleeve until the coupling pin reaches the end of the helical groove 26. Once the coupling pin 28 hits the end of the helical groove 26, further movement by the DC motor and gearbox assembly or other type of pump and valve actuator 66 (FIG. 4) increases torque on the sleeve 24 beyond the threshold, causing the interlock 42 to flex and permit the detent 40 to pass by the bump 48. At the completion of rotation of the sleeve 24 such that its side hole is oriented with the cannula 72 or outlet port 46, the detent 40 moves past the bump 48 in the interlock 42, as shown in FIG. 3B. Another sleeve feature 41 can be provided to engage an electrical switch (e.g., an end-stop switch 90 provided on a printed circuit board 92 and disposed relative to the sleeve and/or end plug 34 to cooperate with the pump measurement device 78 as shown in FIG. 3C).

FIG. 4 is an illustrative system diagram that illustrates example components in an example medication delivery device 10 having an infusion pump such as the pump of 1, 2, 3A, 3B and 3C. The medication delivery device 10 can include an electronics sub-system 52 for controlling operations of components in a fluidics sub-system 54 such as the pump 64 and an insertion mechanism 74 for deploying a cannula 72 for insertion into an infusion site on a patient's skin. A power storage sub-system 50 can include batteries 56, for example, for providing power to components in the electronics and fluidics sub-systems 52 and 54. The fluidics sub-system 54 can comprise, for example, an optional fill port 68 for filling a reservoir 70 (e.g., with medication), although the medication delivery device 10 can be optionally shipped from a manufacture having its reservoir already filled. The fluidics sub-system 54 also has a metering sub-system 62 comprising the pump 64 and a pump actuator 66. As described above, the pump 64 can have two ports 44, 46 and related valve sub-assembly that controls when fluid enters and leaves a pump chamber 38 via the respective ports 44, 46. One of the ports is an inlet port 44 through which fluid such as liquid medication flows from the reservoir 70 into the pump 64 as the result of a pump intake or pull stroke on a pump plunger or piston 30, for example. The other port is an outlet port 46 through which the fluid leaves the pump's chamber 38 and flows toward a cannula 72 for administration to a patient pump as the result of a pump discharge or push stroke on the pump plunger or piston 30. The pump actuator 66 can be a DC motor and gearbox assembly or other pump driving mechanism for controlling the plunger or piston 30 and other related pump parts such as a sleeve 24 that may rotate relative to the translational movement of the pump piston 30. The microcontroller 58 can be provided with an integrated or separate memory device having computer software instructions to actuate, for example, rotation of the sleeve 24 in a selected direction, translational or axial movement of a piston 30 in the sleeve 24 for an aspirate or dispense stroke, and optionally the rotation of the sleeve 24 and piston 30 together during a valve state change as described in the above-referenced WO 2015/157174. As described below, an occlusion detection algorithm in accordance with illustrative embodiment can be provided to the microcontroller 58 to monitor pump measurements and detect when occlusion operating condition occurs relative to the infusion pump.

Regardless of the type of pump mechanism 64 used to aspirate a controlled volume of medication into a pump chamber 38 and to dispense a controlled volume of medication from the pump chamber, the pump 64 has associated therewith an expected pump duration for one or both of the aspirate and dispenses stages or strokes which can be attributed to the pump characteristics. For example, in the illustrative pump assembly 20 shown in FIGS. 1, 2, 3A, 38 and 3C, the pump's duration for aspirating medication into the chamber and for dispensing the medication from the chamber 38 is affected by such pump characteristics as the internal volume of the pump chamber 38, the length or distance of a pump piston stroke, characteristics of port seals provided at the inlet and output ports 44, 46, etc. When the pump pressure is within a designated relative normal range for operation, the pump duration for filling the chamber 38 with a designated amount of fluid (e.g., a desired dosage) and for discharging the designated amount of fluid from the chamber can be determined and used as a baseline for monitoring the pump 64 for normal operating conditions and for determining when an abnormal operating condition has arisen such as due to a leakage of fluid from the pump chamber or an occlusion in the pump fluid path whereby, in either scenario, the designated amount of fluid (e.g., a desired dosage) cannot be delivered from the chamber via a dispense stroke. This can be undesirable since the patient will not be receiving the desired dosage.

As stated above, a typical solution for occlusion detection is to place an additional pressure sensor in the pump control system and report occlusion when the pressure is above a certain threshold. Adding a pressure sensor, however, has the drawbacks of increasing the complexity of the system (e.g., mechanical, electrical, and/or software complexity), increasing system power consumption, and/or increasing pump cost. These drawbacks can be particularly disadvantageous to a wearable pump design wherein all or part of the pump is intended to be disposable once the reservoir 70 is emptied or the pump 64 has been used to a selected amount of time and/or to deliver a selected amount of medication.

In accordance with illustrative embodiments, occlusion detection is accomplished without an additional component such as an occlusion sensor deployed upstream or downstream of the pump 64. When a microcontroller 58 or other processing device for controlling pump operation already performs pump duration measurements for normal operations such as for one or both of aspirate strokes and dispense strokes, the microcontroller 58 can be further controlled to determine when a pump duration measurement is outside a designated range of normal operating conditions and therefore indicates an occlusion, and generate an indication of detected occlusion. The pump 64 and/or the entire medication delivery device 10 can therefore, in turn, be replaced or repaired, thereby ensuring that the patient is receiving the full intended dosage that is provided under normal operating conditions.

When pump duration measurement is implemented for pump operation, occlusion detection can be achieved by adding to the computer software instructions of the microcontroller 58, or a remote device that controls the medication delivery device 10, such operations as monitoring pump duration and determining when a designated pump duration threshold or other criteria for normal pump operating conditions is not met. Thus, occlusion detection is implemented via a software solution, and no hardware changes to the pump are needed. As will be described below, a clear distinction of pump duration exists between the normal and occluded pumps; therefore, the false alarm rate and miss rate are quite low. Therefore, an occlusion detection algorithm configured in accordance with aspects of illustrative embodiments is able to provide reliable occlusion detection results.

Determining a pump duration threshold value or range of values or other metric that indicates occlusion can be performed empirically for a selected type of pump 64, for example. Metrics for a selected type of pump experiencing normal operational pressure can be compared with metrics for the same type of pump except that it is experiencing at least a partial or full occlusion. For example, an occlusion in a downstream path from the occluded pump 64 to its cannula 72 causes pressure in the fluid path of the pump 64 to increase over time. When pressure in the occluded pump exceeds a threshold, the occluded pump eventually begins to leak. Log files of the normal pump and the occluded pump can be generated to obtain their respective histories of pump duration information for aspirate strokes and/or dispense strokes. It is to be understood, however, that a different pump measurement besides pump duration (i.e., duration of an aspirate stroke or a dispense stroke) can be used to determine differences in pump operations during normal and occluded operating conditions and to determine a threshold for monitoring pump operations and distinguishing between a normal operating condition and an occluded operating condition. For example, as described below, a prolonged end-of-stroke switch activation or significant difference in the respective durations of an aspirate stroke and a dispense stroke can be used to detect the occurrence of an occlusion.

Figure 5A:
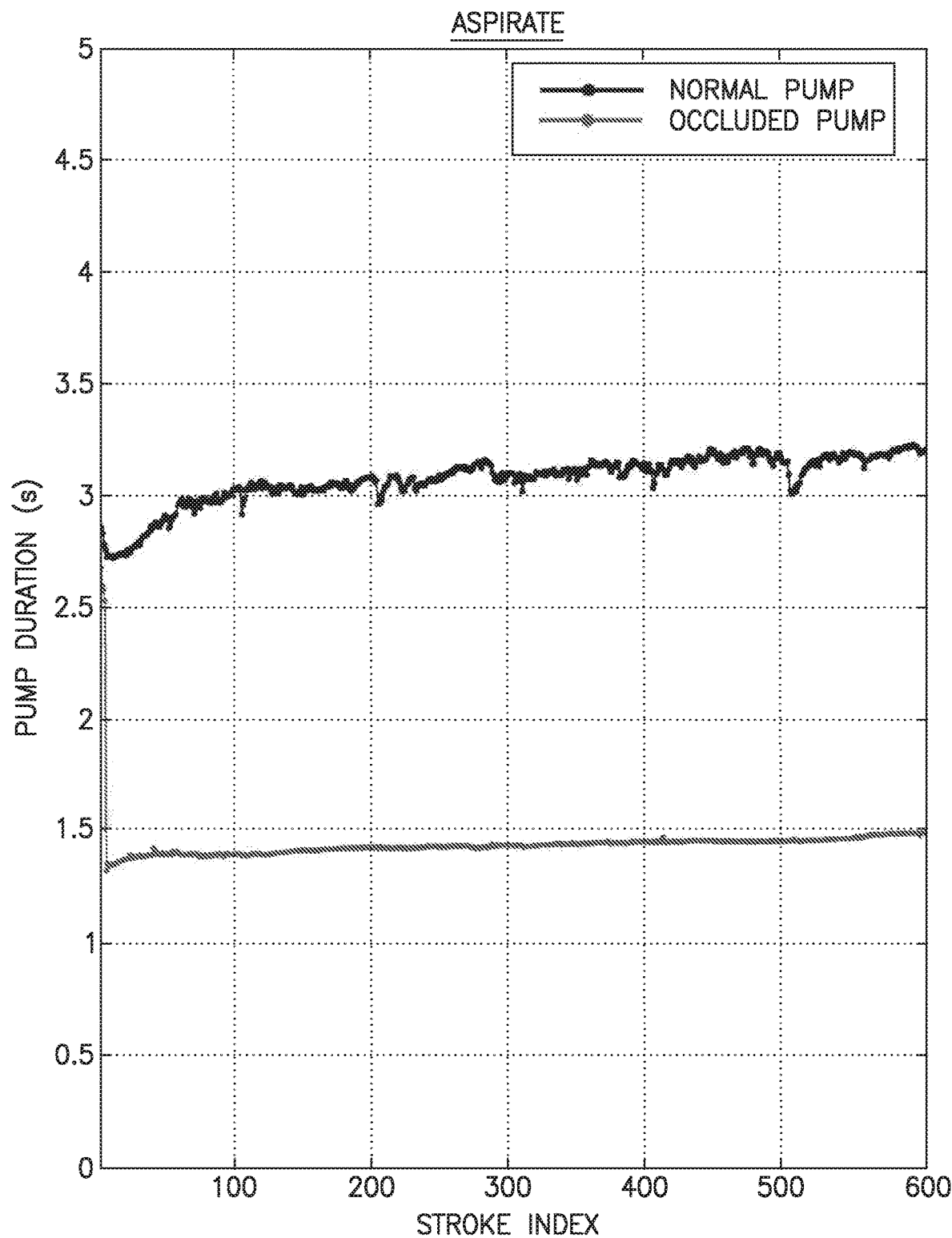
FIGS. 5A and 5B are, respectively, diagrams illustrating pump duration times for a plurality of aspirate operations and a plurality of dispense operations of an example medication delivery device under normal operating conditions.
Figure 5B:
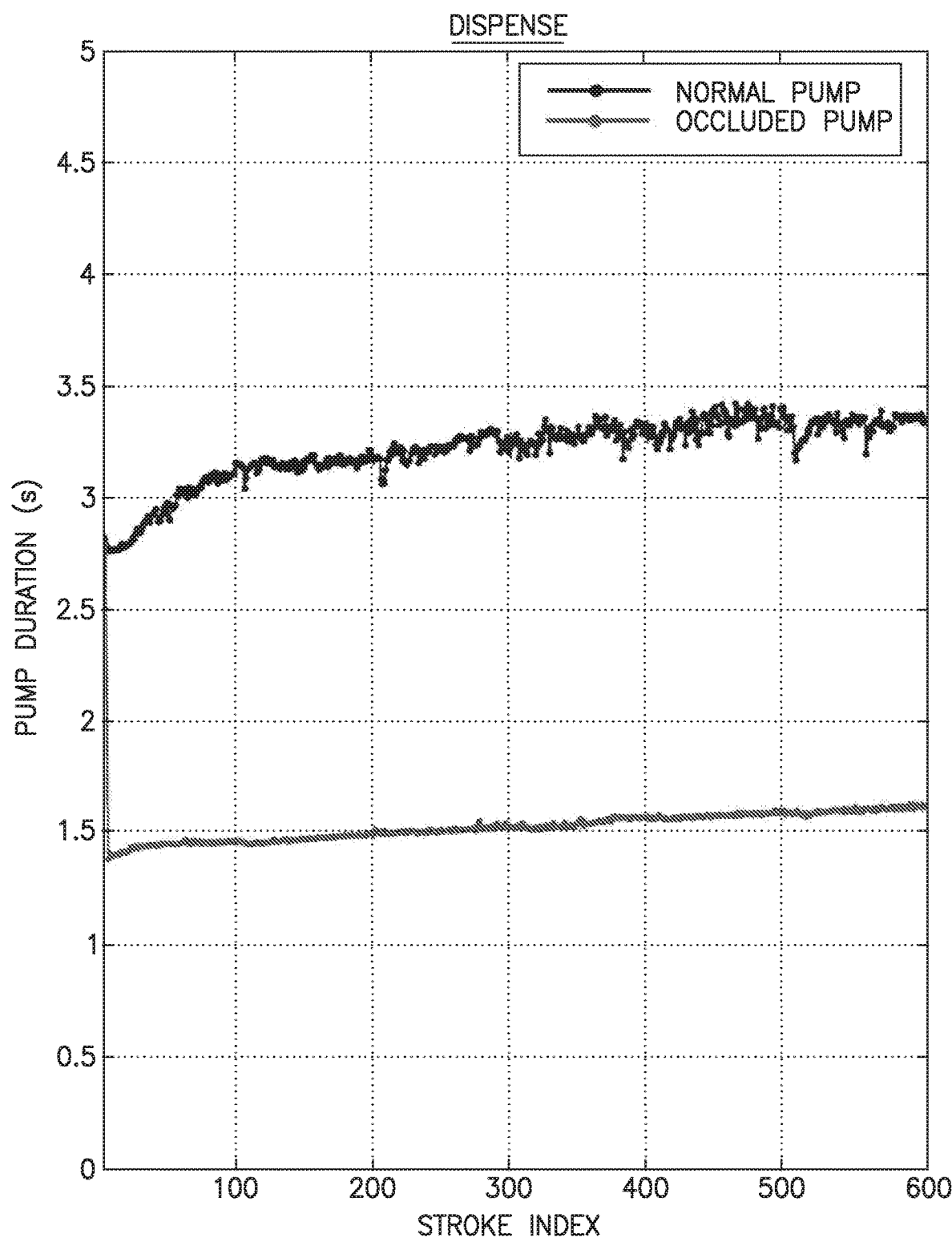

With reference to FIGS. 5A and 5B, the pump duration (e.g., approximately 1.5 seconds on average) of a pump experiencing occlusion is considerably shorter than the pump duration (e.g., on the order of 3-3.5 seconds) of the pump 64 when it is operating under normal conditions, and the phenomenon of shorter pumping duration is related to the pumping mechanism such as the piston 30, sleeve 24, interlock 42 and silicon seals on the inlet and outlet ports 44, 46 described above in connection with FIGS. 1, 2, 3A, 3B and 3C. As described above, different types of pumps 64 can be improved by implementing occlusion sensing in accordance with illustrative embodiments, and different pump components can contribute to the shortened pump during an occlusion condition. The pumps 64 can be rotational metering-type pumps or reciprocating-type pumps or other type of pump that employ pulling in or aspirating fluid from an upstream reservoir, and then discharging or dispensing that fluid to a separate downstream fluid path that leads to the patient.

With reference to the example infusion pump 64 described above in connection with FIGS. 1, 2, 3A, 3B and 3C, the pump's aspirate and dispense strokes, driven by piston 30 translation within the outer plastic sleeve 24, are related to the switching of the pump 64 between the upstream and downstream fluid paths. As the piston 30 is rotated (e.g., by the DC motor and gearbox assembly that is not shown), the piston 30 translates through the sleeve 24, guided by travel of the pin 28 on the piston through a helical slot 26 in the sleeve 24. Once the piston 30 translates fully through the sleeve 24 and completes its aspiration stage or dispensing stage of fluid, it engages with the sleeve 24 directly via the pin 28 in the slot 26, and rotation of the piston 30 and sleeve 24 become coupled. This allows for the sleeve 24 to rotate between upstream and downstream fluid paths and actuate an end of stroke electrical switch 90 or other component associated with the pump measurement device 78 (FIG. 4) and provided on the pump 64 and/or in the medication delivery device 10. During normal operation, the presence of the interlock 42 prevents the piston 30 and sleeve 24 rotation from coupling prior to the piston 30 completing its translation through the sleeve 24. However, if pressure in the downstream fluid path increases beyond a threshold, the piston 30 and sleeve 24 rotation couple and allow for the sleeve 24 to pass under the interlock 42 and actuate the switch 90 (e.g., via a sleeve feature 41 associated with the pump measurement device 78) before the piston 30 has completed its translation through the sleeve. This shortens the pumping duration considerably (e.g., from between 3 and 3.5 seconds during normal conditions to less than 2 seconds during occluded conditions).

Figure 6A:
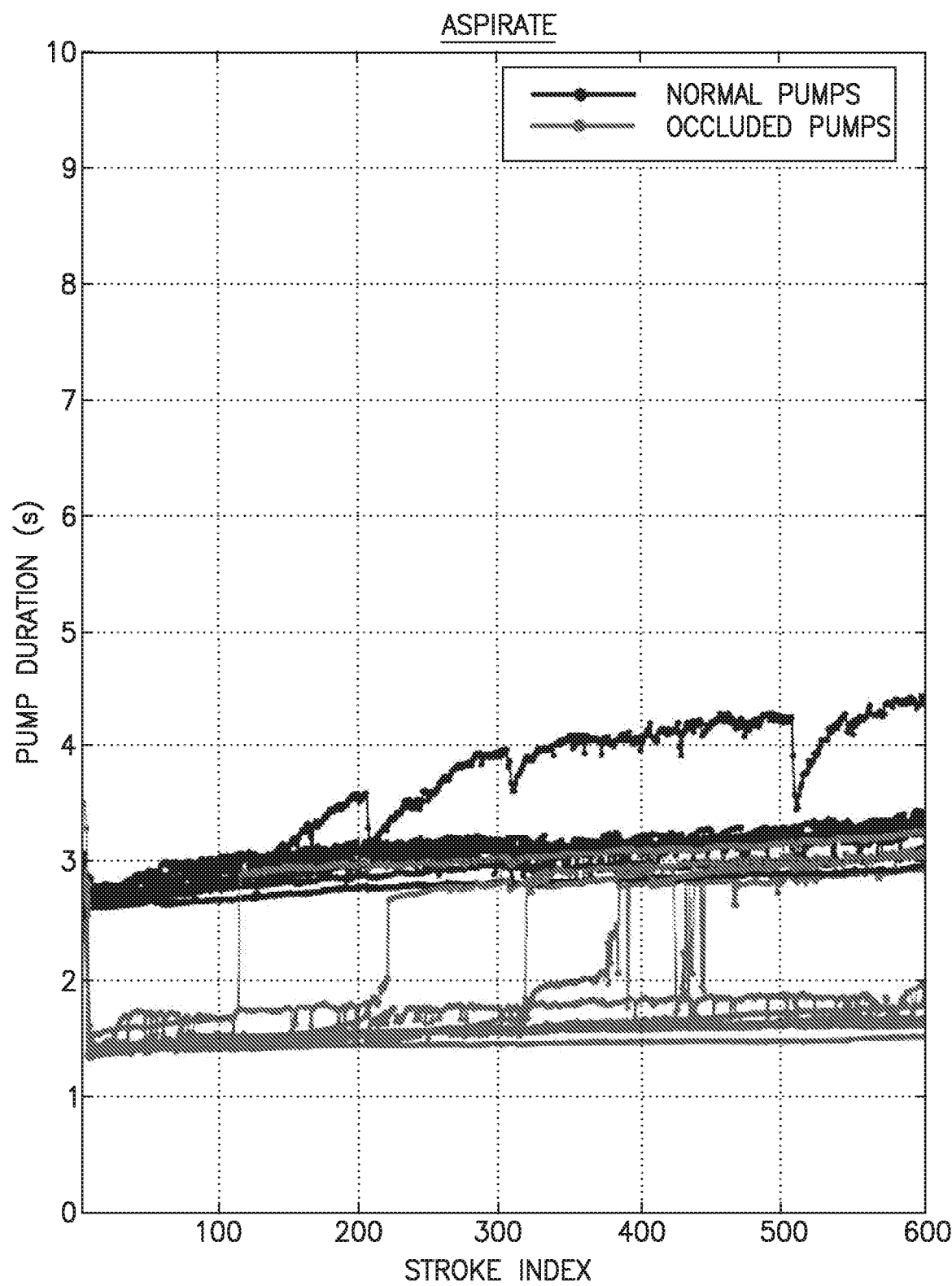
FIGS. 6A and 6B are, respectively, diagrams illustrating pump duration times for a plurality of aspirate operations and a plurality of dispense operations of the same type of medication delivery device used to generate FIGS. 5A and 5B but under occluded operating conditions.
Figure 6B:
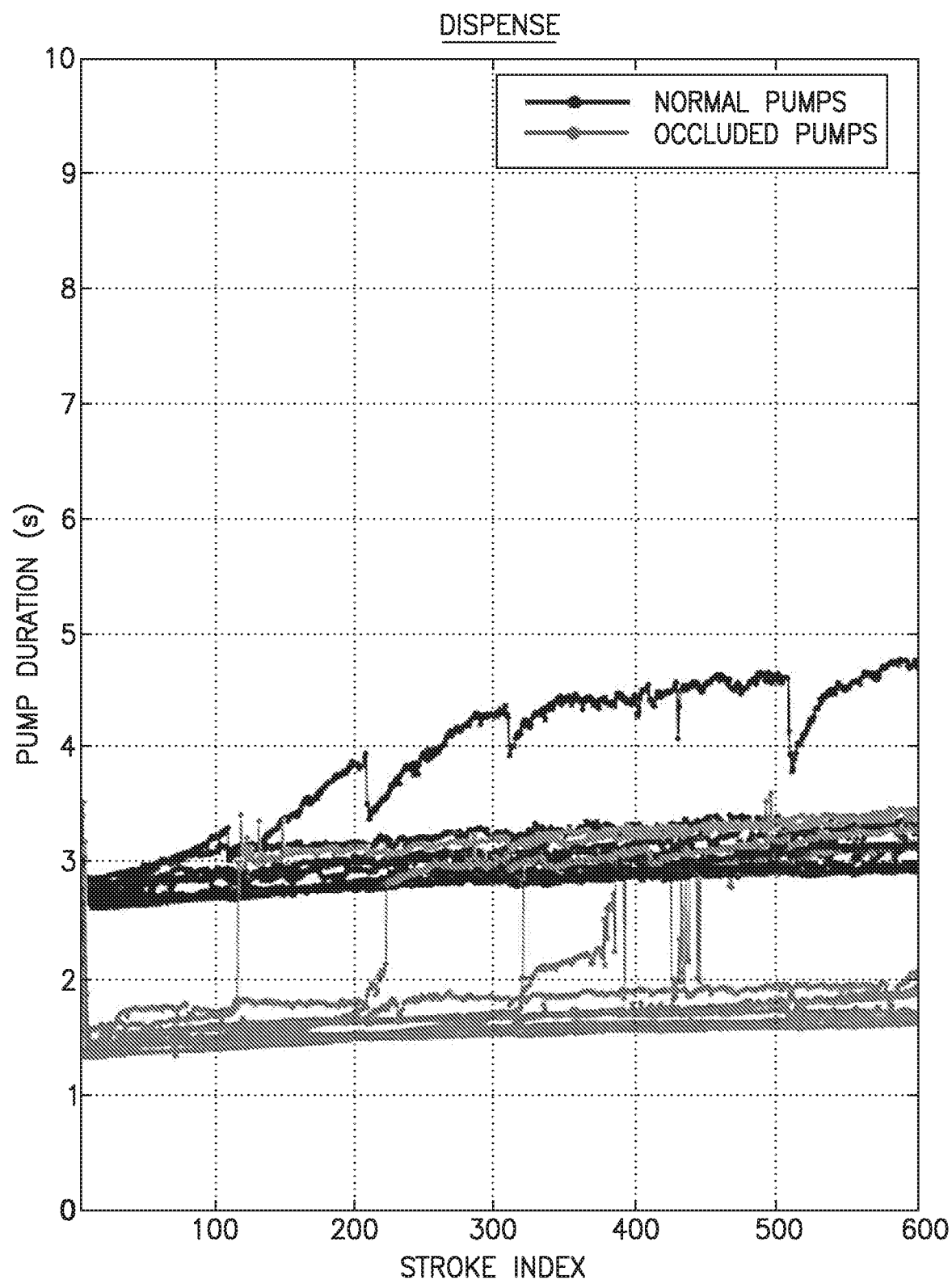

Reference is now made to FIGS. 6A and 6B which show pump duration data from a plurality of similar type pumps 64 over plural pump cycles. For example, log data from 19 pumps that completed finished 600 cycles is shown whereby 10 of the pumps operated under normal conditions, and 9 of the pumps operated under occluded conditions. It can be seen from FIGS. 6A and 6B that all of the occluded pumps had a section of pump duration less than 2 seconds. Some pump durations went back to normal, which may be due to the release of pressure from leaking at the manifold area. The clear distinction of pump duration between the normal operating pump and the pumps experiencing occlusion allows for use of an occlusion detection algorithm based on pump duration.

Figure 7:
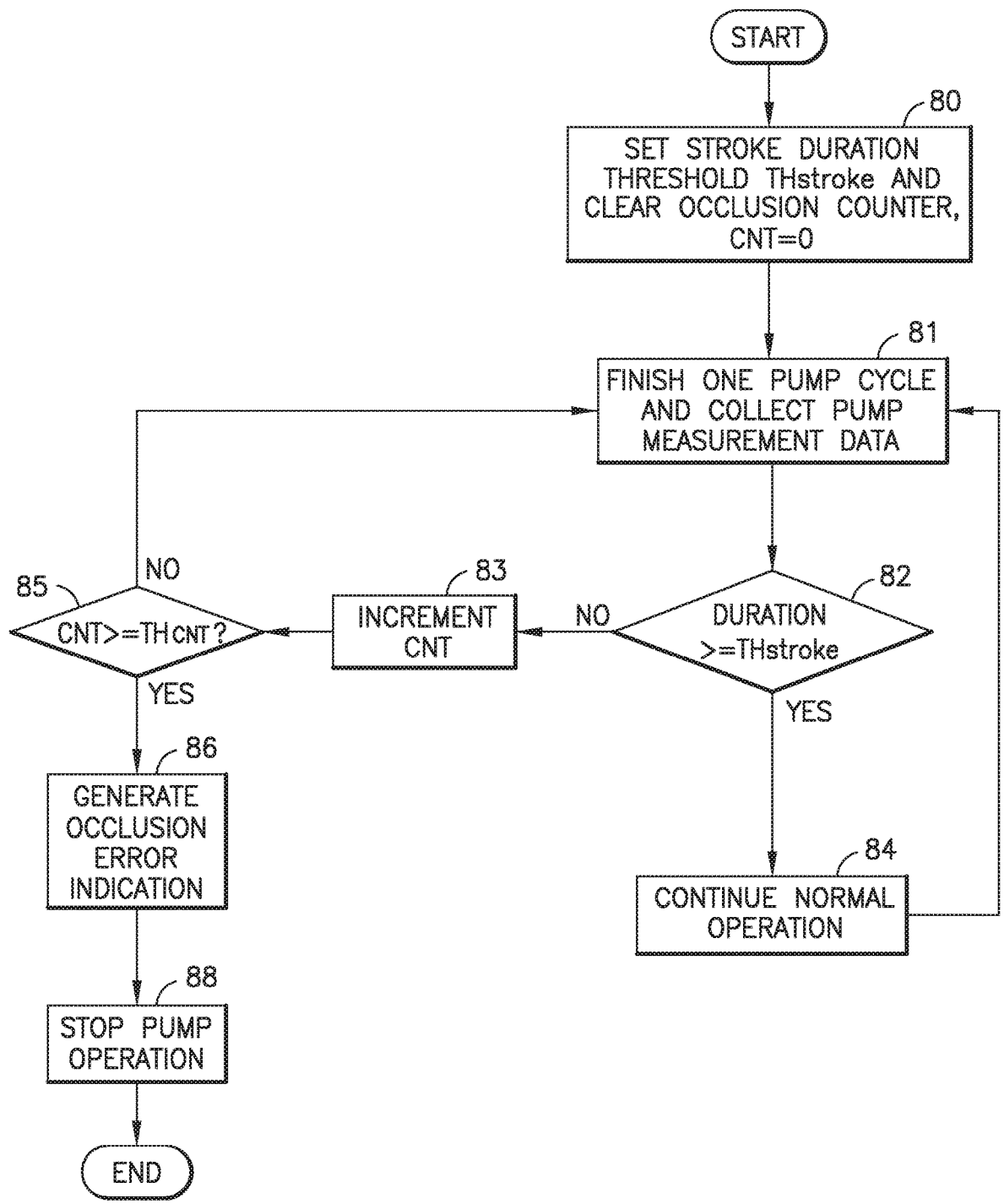
FIG. 7 is a flow chart of illustrative operations of an example medication delivery device that operates in accordance with an occlusion detection algorithm employing stroke duration criteria in accordance with an illustrative embodiment of the present invention.

With reference to FIG. 7, an example occlusion detection process comprises setting a pump measurement threshold or metric such as a stroke duration threshold (block 80), wherein a stroke duration above the threshold indicates normal pump operation and a stroke duration below the threshold indicates occlusion. To set the threshold, pump measurement data is analyzed. For example, aspirate stroke durations and dispense stroke durations can be detected by a limit switch or other pump measurement device 78 (FIG. 4) provided to the pump. In the example pump described with reference to FIGS. 1, 2, 3A, 3B and 3C, stroke or pump durations are determined using a sleeve rotation limit switch or other pump measurement device 78. For example, a microcontroller 58 and other electronic components such as an end-stop switch 90 that cooperates with the sleeve feature 41 can be deployed on a printed circuit board (PCB) 92 associated with the pump 64 or the delivery device 10 in general. End-stop switch activation data can be collected and stored (e.g., via a memory device integral to the microcontroller 58 or implemented as a separate component on the PCB 92). The microcontroller 58 can be provided with an occlusion detection algorithm for processing the end-stop switch activation data to determine if an occlusion has occurred. In accordance with another illustrative embodiment, the end-stop switch activation data can be provided (e.g., wirelessly or via wireline connection) from the pump 64 to another device having an occlusion detection algorithm such as a hand-held remote controller for the pump 64 or a non-dedicated computing device (e.g., mobile phone, personal computer (PC), laptop or other portable computing device) provided with software or app comprising the occlusion detection algorithm.

Pump measurement data is obtained for one or more of the same type of pump operating under normal conditions, and for one or more of the same type of pump operating under occluded conditions, as illustrated above in FIGS. 5A and 5B and in FIGS. 6A and 6B. The pump measurement data for these two groups of pumps can be averaged or otherwise summarized or categorized, and then analyzed to determine the degree of difference between the pump measurements for normal operating pumps and the pump measurements for occluded pumps. A threshold or other metric is determined to be a value or a range of values with a margin(s) above and/or below which normal pump measurements will not fall. The value, or range of values, and/or margin can be designated by a user, or automatically determined based on the pump measurement data obtained from the pump. As described above, the pump measurement data is data that is generated and monitored during the course of normal pump activity and therefore is not an added operation or require an additional component that increases the complexity of the pump.

With continued reference to FIG. 7, once the pump measurement metric (e.g., stroke duration threshold) is set, the microcontroller 58 in the medication delivery device 10 is controlled by the occlusion detection algorithm to obtain pump measurement data (e.g., stroke duration data) for the pump (block 81), and to compare the stroke duration data to the pump measurement metric during various pump stages or cycles of operation such as for each pump cycle (block 82). When the stroke duration data meets the pump measurement metric (e.g., is greater or equal to a $Th_{stroke}$ of 2 seconds for the pump 64), the pump is determined to be operating normally (block 84). When the stroke duration data fails to satisfy the pump measurement metric (e.g., is below the occlusion detection threshold (e.g., is less than a $Th_{stroke}$ of 2 seconds for the pump 64)), then the pump is determined to be experiencing an occlusion condition. A counter is incremented (block 83) when a threshold $Th_{stroke}$ for normal operation is not met. With reference to block 85, when the counter reaches a selected value (e.g., the counter value of 8 corresponding to 8 pump cycles wherein a threshold $Th_{stroke}$ for normal operation is not met), then occlusion is detected. The total number of cycles during which the selected number of cycles is reached before occlusion is indicated can be designated such as 8 consecutive cycles of 8 cycles or within a designated number of cycles (e.g., 20 cycles). The microcontroller 58 can be configured by the occlusion detection algorithm to generate an optional indication of detected occlusion error (block 86), and to automatically stop operation of the pump and/or the medication delivery device 10, and/or generate an optional indication to the user to cease using the pump (block 88). If the counter, after being incremented per block 83, has not yet reached the selected counter value, then the pump measurement data continues to be collected per block 81. Since the occlusion detection algorithm is based on pump duration or other pump measurement data that has already been implemented in the pump, occlusion detection is achieved by checking pump duration or other measurement data in the software against a selected threshold or metric. Accordingly, a software-only solution is provided for occlusion detected, obviating the need for any hardware changes.

The example pump 64 described in connection with FIGS. 1, 2, 3A, 3B and 3C uses one or more on/off limit switches to determine the state of the system at the limits of rotational travel. For example, multiple stage pumps (i.e., a pump that aspirates fluid to fill a chamber during one stage and then discharges the pump chamber in the next stage) can employ an end-stop switch of some type for each stage to detect when the piston and/or a sleeve or other pump component reaches a predetermined position corresponding to a complete aspirate or dispense position. It is to be understood, however, that different mechanisms or other pump measurement device 78 can be used to determine the pump measurement (e.g., pump duration) besides an interlock 42 and sleeve rotational limit switch (e.g., end-stop switch) 90. Alternatively, the pump 64 can employ one or more optical sensors, or an encoder with optical switch to determine positions of pump components at their respective end-stop positions for complete aspiration and/or dispensing.

Thus, as described with reference to FIG. 7 and in accordance with illustrative embodiments of the invention, determination of a time needed to fill the chamber, and a time needed to discharge a desired amount of fluid from the chamber, is performed, at least the discharge times of each stroke is measured, and, when a selected number of discharge times fails to exceed a designated amount (e.g., the stroke duration shortens over a designated number of pump cycles), an indication is generated to indicate that an occlusion is detected.

In accordance with another illustrative embodiment, occlusion detection is performed by monitoring duration of activation or triggering of a pump end-stop or limit switch, as will be described below with reference to FIG. 9. Processing monitored data related to the detected duration of activation or triggering of a pump end-stop or limit switch to determine if an occlusion in the pump 64 has occurred can be performed singly or in combination with monitoring for short pump stroke duration as described above in connection with FIG. 7.

As explained above, during normal operation, the presence of the interlock 42 prevents the piston 30 and sleeve 24 rotation from coupling prior to the piston 30 completing its translation through the sleeve 24. However, as pressure in the downstream fluid path builds (i.e., during an occlusion), the piston 30 and sleeve 24 rotation can couple prematurely; that is, the sleeve 24 rotates prematurely before an intended rotation during a valve state change, for example, when the sleeve 24 rotates at the end of a complete piston stroke and without axial motion to align its side port with a corresponding one of the ports 44, 46 during normal operation of the pump). This premature rotation coupling of the piston 30 and sleeve 24, in turn, allows for the sleeve 24 to pass under the interlock 42 and trigger the switch 78 before the piston 30 has completed its axial translation through the sleeve. This shortens the pumping duration (e.g., measured as time period or duration between pump motor startup and end-stop switch signal) considerably as explained above in connection with FIG. 7. In addition, another pump operation characteristic that can be monitored for occlusion detection is the duration that a pump measurement device 78 and its associated switch 90 is in an activated or triggered mode of operation or otherwise indicates the beginning of a state of activation.

In some instances, pump duration in an occluded pump system can remain normal and not decrease as expected; therefore, monitoring for another pump measurement parameter or characteristic increases occlusion detection accuracy. For example, while the pump sleeve 24 rotates prematurely as anticipated due to the occlusion in the pump system, and as soon as the pump sleeve opens to the upstream fluid path (and before the end-of-stroke signal from the switch 90), the piston can begin advancing and dispensing the fluid payload back into the upstream fluid path. Because both the piston 30 and sleeve 24 can rotate through their full range of angular position, the total pump operation time remains constant both with and without an occlusion. On the other hand, since the piston 30 is now rotating and translating through the sleeve 24 after the sleeve has rotated over the upstream channel, the end-stop switch 90 is now being triggered for an extended period of time. Thus, occlusion detection can comprise monitoring for prolonged or extended end-stop of limit switch activation or triggering separately, or in addition to, monitoring for shortened pump stroke duration in accordance with illustrative embodiments.

Figure 8A:
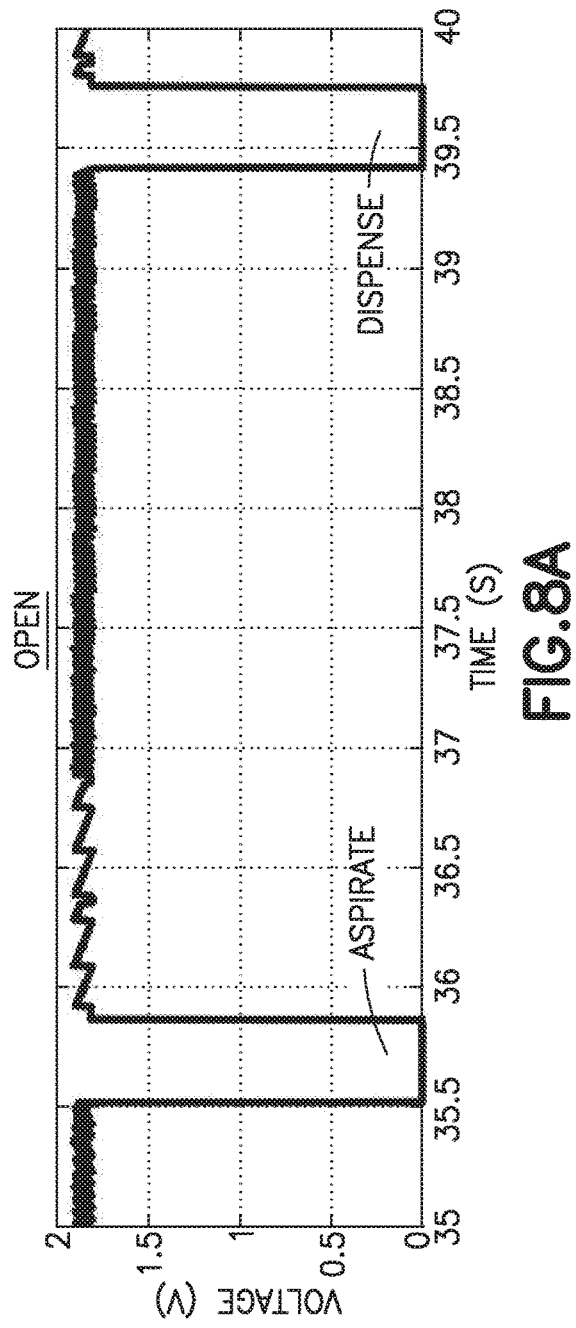
FIGS. 8A and 8B depict, respectively, example end-stop or limit switch activation data during normal and occluded operation of an illustrative pump.
Figure 8B:
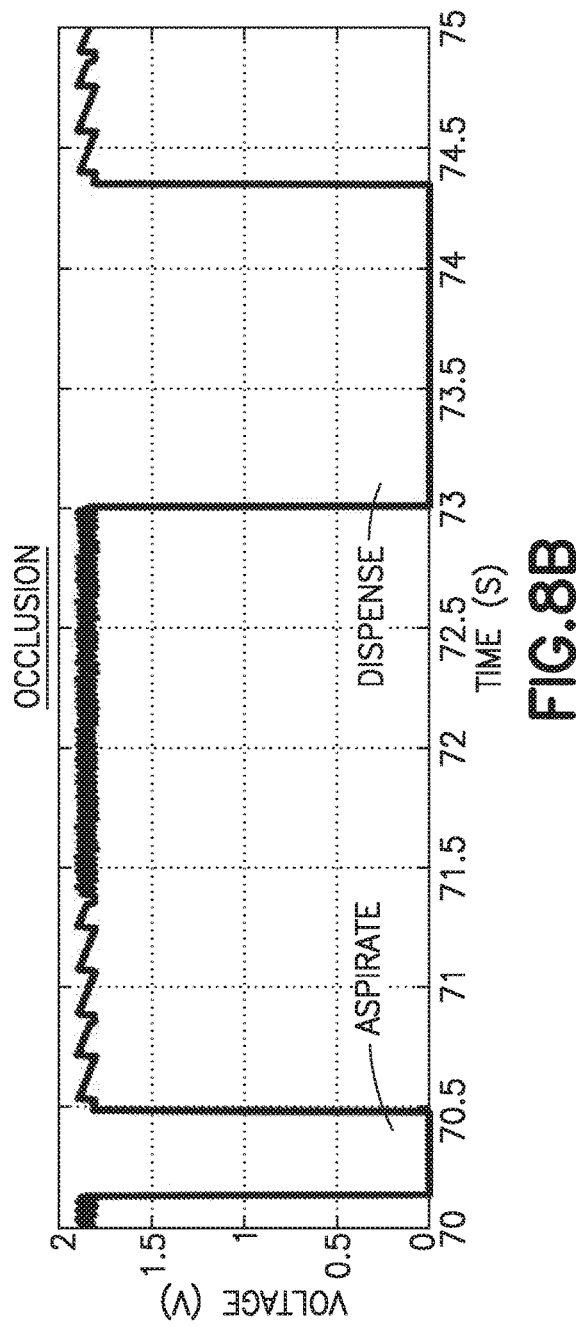

To further illustrate how activation or triggering of a pump measurement device can be prolonged as a result of an occlusion, reference is made to the example pump 64 described in accordance with the illustrative embodiment depicted in FIGS. 1, 2, 3A, 3B and 3C. During normal pump 64 operation, when the end-stop switch 90 is first hit and dragged by the pump sleeve 24 (e.g., via the sleeve feature 41 that engages with the end-stop switch 90) and therefore triggered, the end-stop switch 90 produces a drop in its end-stop switch voltage signal from 1.8 V to 0 V that is provided to the microcontroller 58. Only after the switch 90 is released (e.g., by disengagement of the sleeve feature 41) and springs back to center does the end-stop switch voltage return back to 1.8 V. When, in some instances, the side port of the sleeve 24 opens to the upstream fluid path (e.g., aligns with the input port 44) before the piston 30 has completed its axial translation and before the end-stop switch 90 has been disengaged by the sleeve feature 41, and when the pressure in the upstream fluid path is low, the piston 30 can begin to advance and translate through the sleeve 24, emptying pump contents into the upstream fluid path while the end-stop switch 90 is in a mid-trigger state. The net result is that the end-stop switch 90 activation signal (e.g., voltage drop) occurs for an extended period of time. This pump occlusion characteristic is shown in FIGS. 8A and 8B which illustrate, respectively, a normal duration of switch 90 activation (e.g., 0 volts) of less than 0.5 seconds, and an extended end-stop or limit switch 90 activation (e.g., 0 volts) of almost 1.5 seconds.

There are several reasons why some pumps 64 may exhibit a shorter overall pump duration (e.g., when the piston 30 fails to advance), while some pumps 64 may exhibit an increase in end-stop switch 90 activation signal duration (e.g., when the piston 30 advances over the upstream fluid path). For example, alignment of the switch 90 on the PCB 92 with the related pump components (e.g., interlock 42, detent 40 and sleeve feature 41) may allow for some variability in what sleeve angular position releases the end-stop switch 90 and thus when the end-stop switch activation signal is generated and provided to the microcontroller 58. Additionally, high pressure in the upstream fluid path from larger insulin reservoir fill volumes may prevent the piston 30 from advancing over the upstream fluid path (e.g., resulting in a shorter pumping duration), while lower pressure in the upstream fluid path from lower insulin reservoir fill volumes may allow the piston 30 to advance over the upstream fluid path (e.g., resulting in longer or extended end-stop or limit switch activation or "trigger" duration).

Figure 9:
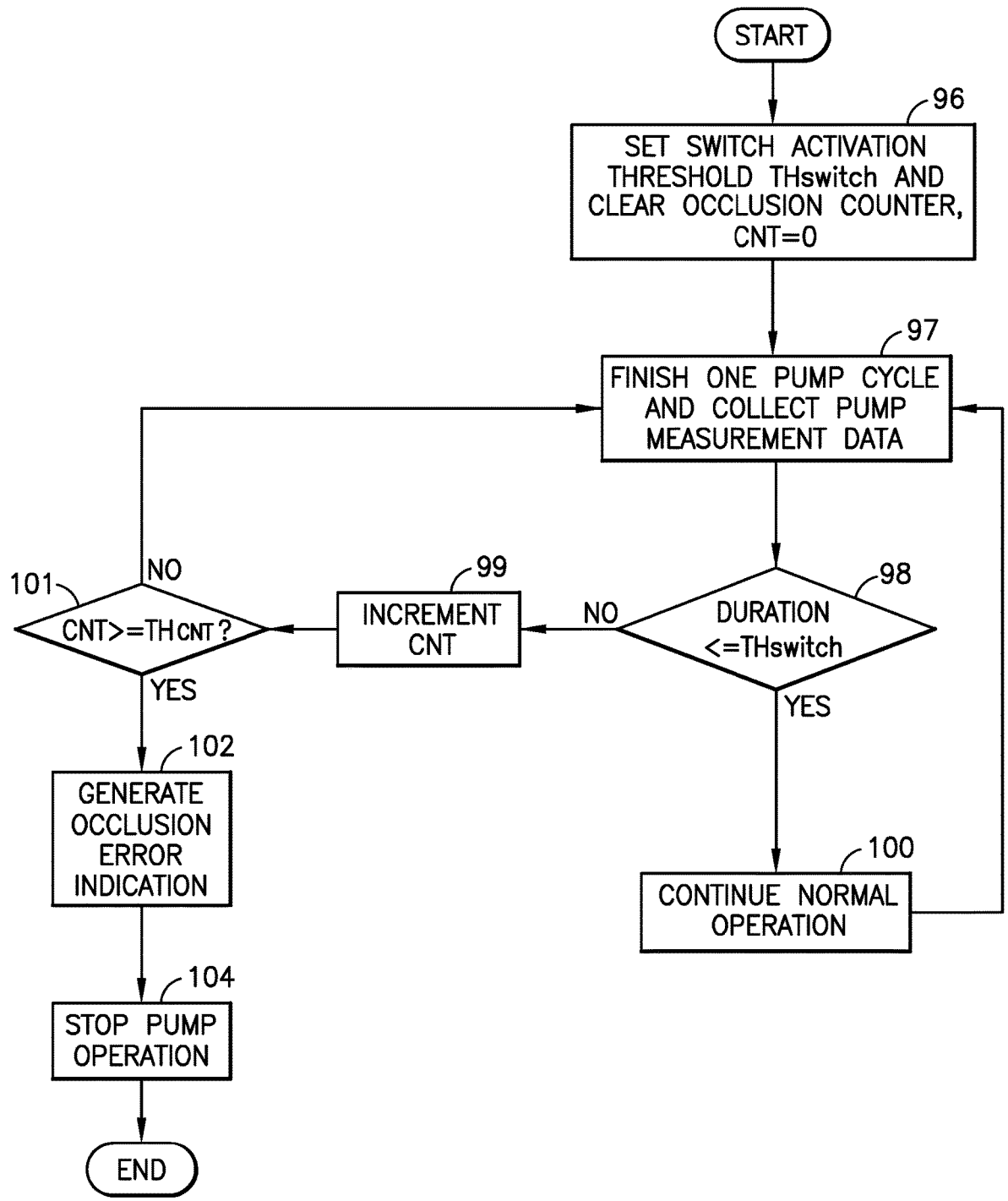
FIG. 9 is a flow chart of illustrative operations of an example medication delivery device that operates in accordance with an occlusion detection algorithm employing end-stop or limit switch activation duration criteria in accordance with an illustrative embodiment of the present invention.

With reference to FIG. 9, an example occlusion detection process comprises setting a pump measurement threshold or metric such as a switch activation duration threshold (block 96), wherein a switch activation duration below the threshold indicates normal pump operation and a switch activation duration above the threshold indicates occlusion. To set the threshold, pump measurement data can be analyzed. For example, a number of the same pumps 64 can be tested with a similar occlusion condition to collect pump measurement data related to an exhibited significant increase in the duration of a pump measurement parameter such as the end-stop switch signal voltage drop when the pump is occluded. In the case of example empirical measurements for the pump 64 in FIGS. 1, 2, 3A, 3B and 3C, switch activation durations during an occlusion measured approximately 1.5 seconds, which is commensurate with the expected amount of time for the piston 30 to translate fully through the sleeve 24. Accordingly, the occlusion detection algorithm can be configured to log end-stop switch 90 signal duration in accordance with software instructions (e.g., in the microcontroller 58), and compare the logged switch 90 activation durations against a threshold value (e.g., $Th_{switch}$>1.0 second(s)) to determine if an occlusion is present or not, as indicated in block 98 of FIG. 9. For example, end-stop or pump limit switch activation data can be collected and stored (e.g., via a memory device integral to the microcontroller 58 or implemented as a separate component on the PCB 92). The microcontroller 58 can be provided with an occlusion detection algorithm for processing the end-stop switch activation data to determine if an occlusion has occurred. In accordance with another illustrative embodiment, the end-stop switch activation data can be provided (e.g., wirelessly or via wireline connection) from the pump 64 to another device having an occlusion detection algorithm such as a hand-held remote controller for the pump 64 or a non-dedicated computing device (e.g., mobile phone, personal computer (PC), laptop or other portable computing device) provided with software or app comprising the occlusion sensing algorithm. The switch activation duration data for occluded pumps can be averaged or otherwise summarized or categorized, and then analyzed to determine the degree of difference between similar pump measurements for normal operating pumps and the pump measurements for the occluded pumps. The threshold (e.g., $Th_{switch}$) or other metric is determined to be a value or a range of values with a margin(s) above and/or below which normal pump measurements will not fall. The value, or range of values, and/or margin can be designated by a user, or automatically determined based on the pump measurement data obtained from the pump. As described above, the pump measurement data such as switch activation duration is data that is generated and monitored during the course of normal pump activity and therefore does not require an additional component that increases the complexity of the pump.

With continued reference to FIG. 9, once the pump measurement metric (e.g., switch activation duration threshold) is set, the microcontroller 58 in the medication delivery device 10 is controlled by the occlusion detection algorithm to obtain pump measurement data (e.g., switch activation duration data) for the pump 64 (block 97), and to compare the switch activation duration data to the pump measurement metric during various pump stages or cycles of operation such as for each pump cycle (block 98). When the switch activation duration data meets the pump measurement metric (e.g., is less than or equal to a $Th_{switch}$ of 1.0 seconds), the pump is determined to be operating normally (block 100). When the switch activation duration data fails to satisfy the pump measurement metric (e.g., is greater than the occlusion detection threshold $Th_{switch}$ of 1.0 seconds), than the pump is determined to be experiencing an occlusion condition. A counter is incremented (block 99) when a threshold $Th_{switch}$ for normal operation is not met. With reference to block 101, when the counter reaches a selected value (e.g., the counter value of 8 corresponding to 8 pump cycles wherein a threshold $Th_{switch}$ for normal operation is not met), then occlusion is detected. The total number of cycles during which the selected number of cycles is reached before occlusion is indicated can be designated such as 8 consecutive cycles of 8 cycles or within a designated number of cycles (e.g., 20 cycles). The microcontroller 58 can be configured by the occlusion detection algorithm to generate an optional indication of detected occlusion error (block 102), and to automatically stop operation of the pump 64 and/or the medication delivery device 10, and/or generate an optional indication to the user to cease using the medication delivery device 10 (block 104). If the counter, after being incremented per block 99, has not yet reached the selected counter value, then the pump measurement data continues to be collected per block 97. Since the occlusion detection algorithm is based on pump duration data or other pump measurement data that has already been implemented in the pump, occlusion detection is achieved by checking pump duration or other measurement data in the software against a selected threshold or metric. Accordingly, a software-only solution is provided for occlusion detected, obviating the need for any hardware changes.

In accordance with another illustrative embodiment of the present invention, a third pump characteristic is monitored to detect an occlusion in a medication delivery device 10, as will be described below in connection with FIG. 13. For example, testing a selected pump 64 under occluded conditions revealed that, if occlusion happens when the medication delivery device 10 was new, the pump 64 tended to have short stroke duration or long end-stop duration as described above in connection with FIGS. 7 and 9, respectively. After the pump went through many cycles, however, test data indicated that it tended to leak at the joint area 49 between the manifold seal 47 and the sleeve 24, as illustrated in FIG. 3B. The reasons why there was excessive leaking after certain pump cycles was likely the combination of the wear and tear of the seal caused by the repetitive pumping motion and the high internal pressure caused by occlusion. In other words, when the pump 64 is new and the seal 47 is strong enough to tolerate the high pressure introduced by occlusion, the pump will likely exhibit a short stroke duration or long end-stop duration (e.g., prolonged limit switch activation duration) during occlusion. After some pump cycles, however, the seal is not strong enough to tolerate the high pressure introduced by occlusion, the pump 64 may leak through the weakest link of the downstream fluid path, which can be the seal 49 between the manifold 47 and the sleeve 24. Since the fluid in the pump chamber 38 is forced through the leakage path by the high internal pressure introduced by occlusion, the pump motor (not shown) needs to provide more energy to push the fluid through. As a result, the dispense stroke duration during occlusion is longer than in normal operation.

FIGS. 12A, 12B, 12C and 12D show a few examples from a bench occlusion test of a selected type of pump such as pump 64 described with respect to FIGS. 1, 2, 3A, 3B and 3C. FIGS. 12A, 12B, 12C and 12D illustrate a long dispense duration related to the leaking caused by occlusion. For four medication delivery devices 10, each plot in FIGS. 12A, 12B, 12C and 12D corresponds to one medication delivery device 10. Each medication delivery device 10 was filled, for example, with 300 U fluid, and delivered 50 U open, 2 U clamped, and 2 U open. It can be seen from these plots that, when the medication delivery devices 10 are occluded, the dispense stroke duration increases, while the aspirate stroke duration stays relatively the same. Accordingly, this pump characteristic can be used to detect leaking caused by occlusion.

In accordance with an aspect of an illustrative embodiment of the present invention, an occlusion detection algorithm as described above can employ a pump duration difference between the dispense stroke and the aspirate stroke. For example, with reference to block 108 in FIG. 13, a stroke difference threshold ($Th_{delta}$) can be determined as follows:

Step 1: At the end of priming, calculate the average duration difference between the aspirate stroke and the dispense stroke, defined as $$D0 = \frac{1}{n}\sum_{i=1}^{n} [\text{Dispense}(i) - \text{Aspirate}(i)],$$

where n is number of strokes used to get the average difference. As an example, n=3 is used for the illustrative embodiment but it is to be understood that this number may vary depending on the specific pump design.

Step 2: For each pump cycle after priming, collect pump measurement data (e.g., duration difference between the aspirate stroke and the dispense stroke) for the pump 64 (block 109), and compare the duration difference data to a pump measurement metric (block 110), for example, as follows:
1) Calculate duration difference: Di=Dispense−Aspirate;
2) Subtract D0 from Di: D'i=Di−D0; and
3) Check whether D'i D'i−1, and D'i−2 are less than a given threshold (e.g., 0.13 seconds), as indicated in block 110 of FIG. 13. If yes, then normal pump operation can continue per block 112 in FIG. 13. If not, then leaking is detected and the pump may be determined to be experiencing an occlusion condition. A counter is incremented (block 111) when a threshold $Th_{delta}$ for normal operation is not met. With reference to block 113, when the counter reaches a selected value (e.g., the counter value of 8 corresponding to 8 pump cycles wherein a threshold $Th_{delta}$ for normal operation is not met), then occlusion is detected and an occlusion indication can be generated per block 114 and pump operation can be terminated per block 116. If the counter, after being incremented per block 111, has not yet reached the selected counter value, then the pump measurement data continues to be collected per block 109. The total number of cycles during which the selected number of cycles is reached before occlusion is indicated can be designated such as 8 consecutive cycles of 8 cycles or within a designated number of cycles (e.g., 20 cycles). Even though three consecutive dispense strokes are used in the illustrative embodiment, this number may vary depending on the variation of the pump duration over time. The duration differences $D_{0,1, \ldots, x}$ can be averaged or otherwise summarized or categorized, and then analyzed to determine the degree of difference between the pump measurements (e.g., aspirate stroke and dispense stroke duration differences) for normal operating pumps and the pump measurements for occluded pumps, and/or with respect to a threshold or other metric $Th_{delta}$.

Figure 10:
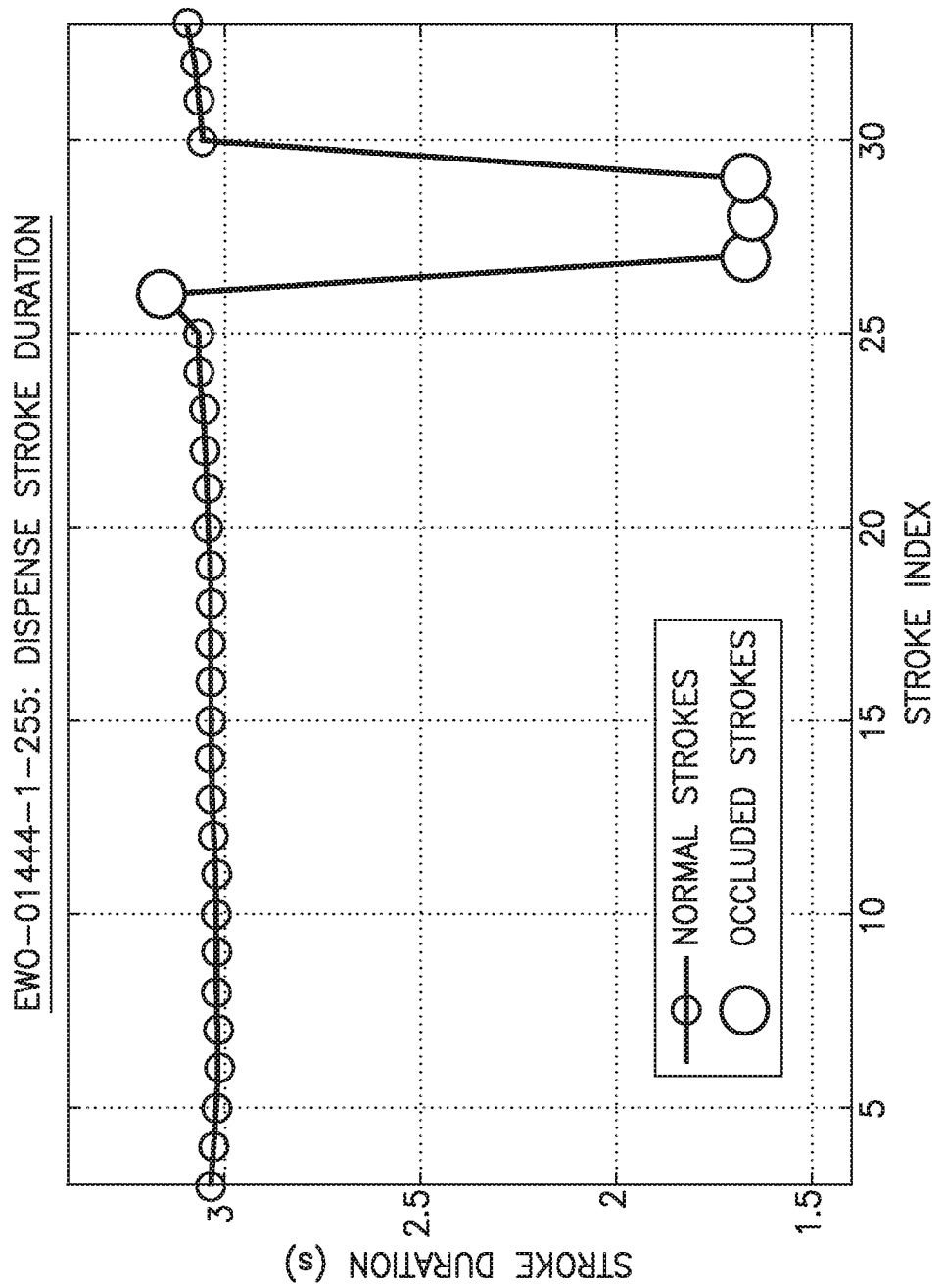
FIG. 10 depicts example pump measurement data indicating a short dispense stoke duration (e.g., such as when the pump piston is not able to move during an occlusion)
Figure 11:
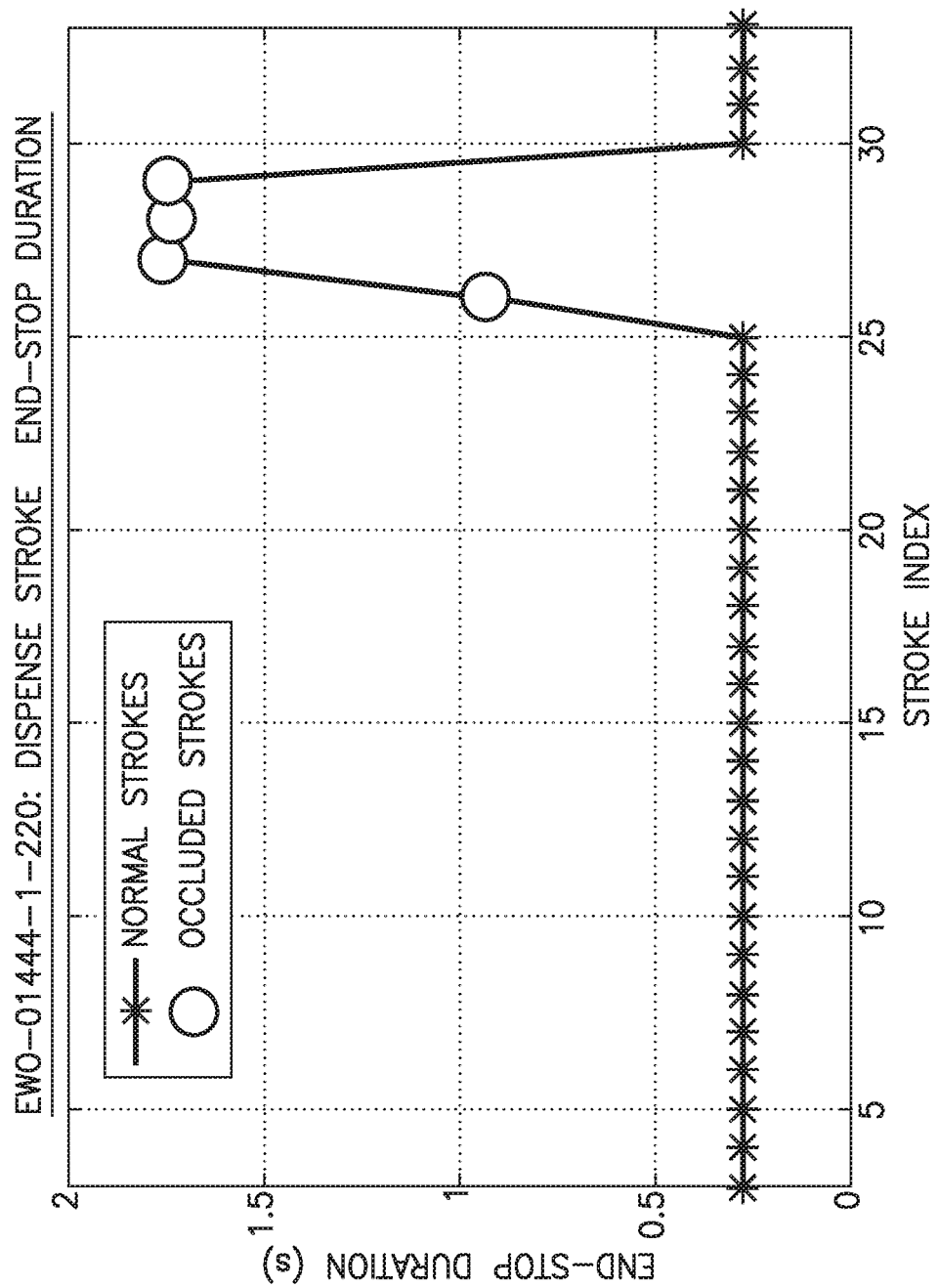
FIG. 11 depicts example pump measurement data indicating an extended end-stop or limit switch activation duration (e.g., such as when pumping back to the pump reservoir occurs due to an occlusion)
Figure 12A:
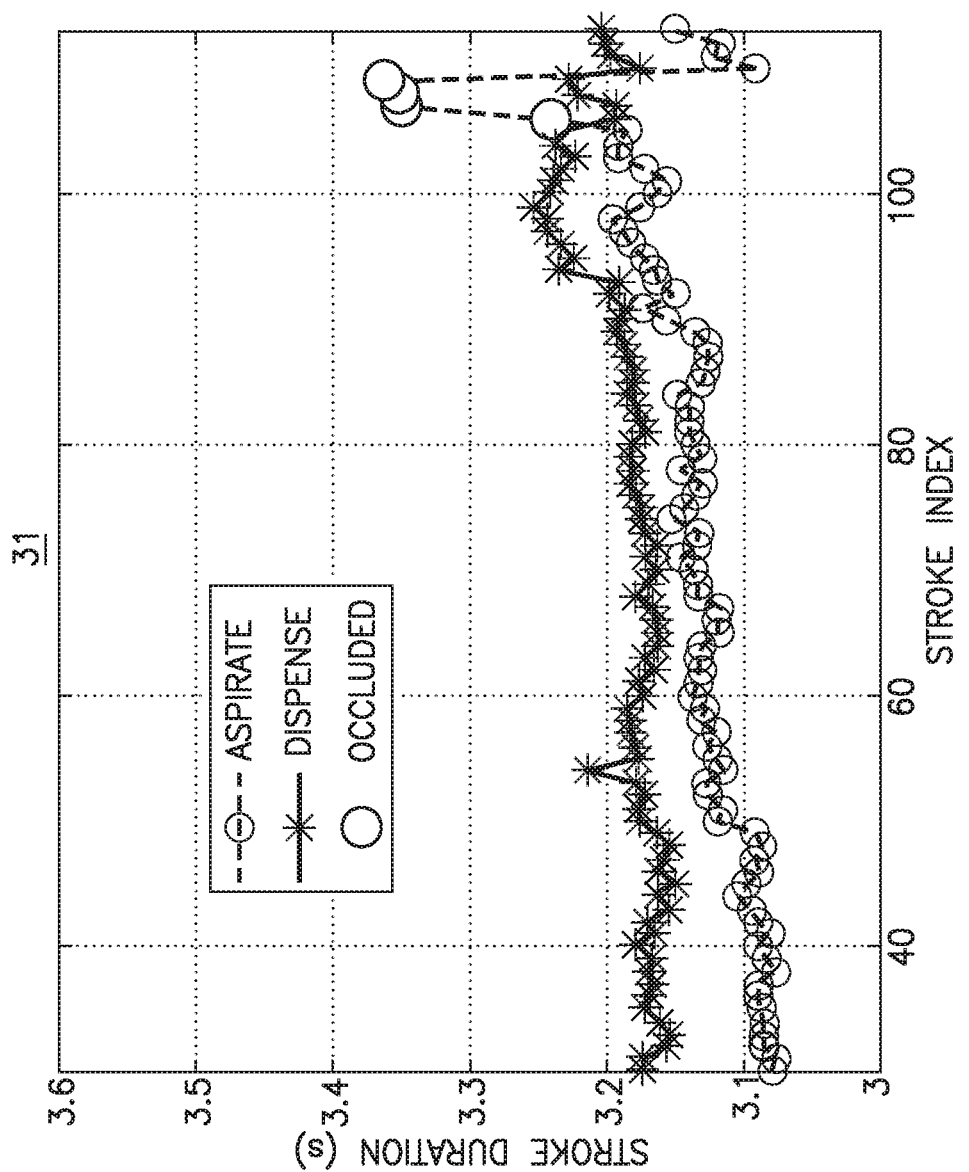
FIGS. 12A, 12B, 12C and 12D depict pump measurement data from respective pumps indicating long dispense stroke duration relative to aspirate stroke duration (e.g., such as when leaking occurs due to an occlusion)
Figure 12B:
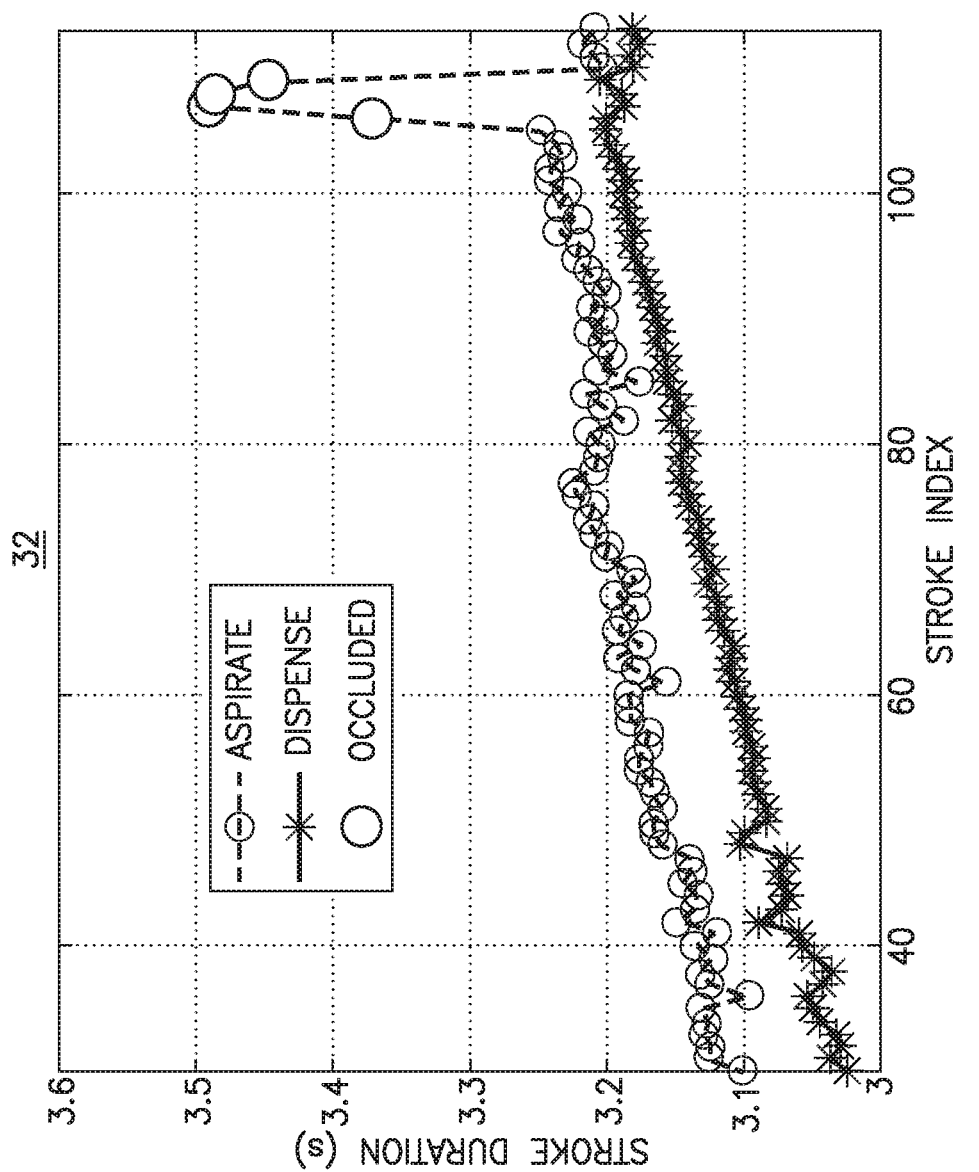
Figure 12C:
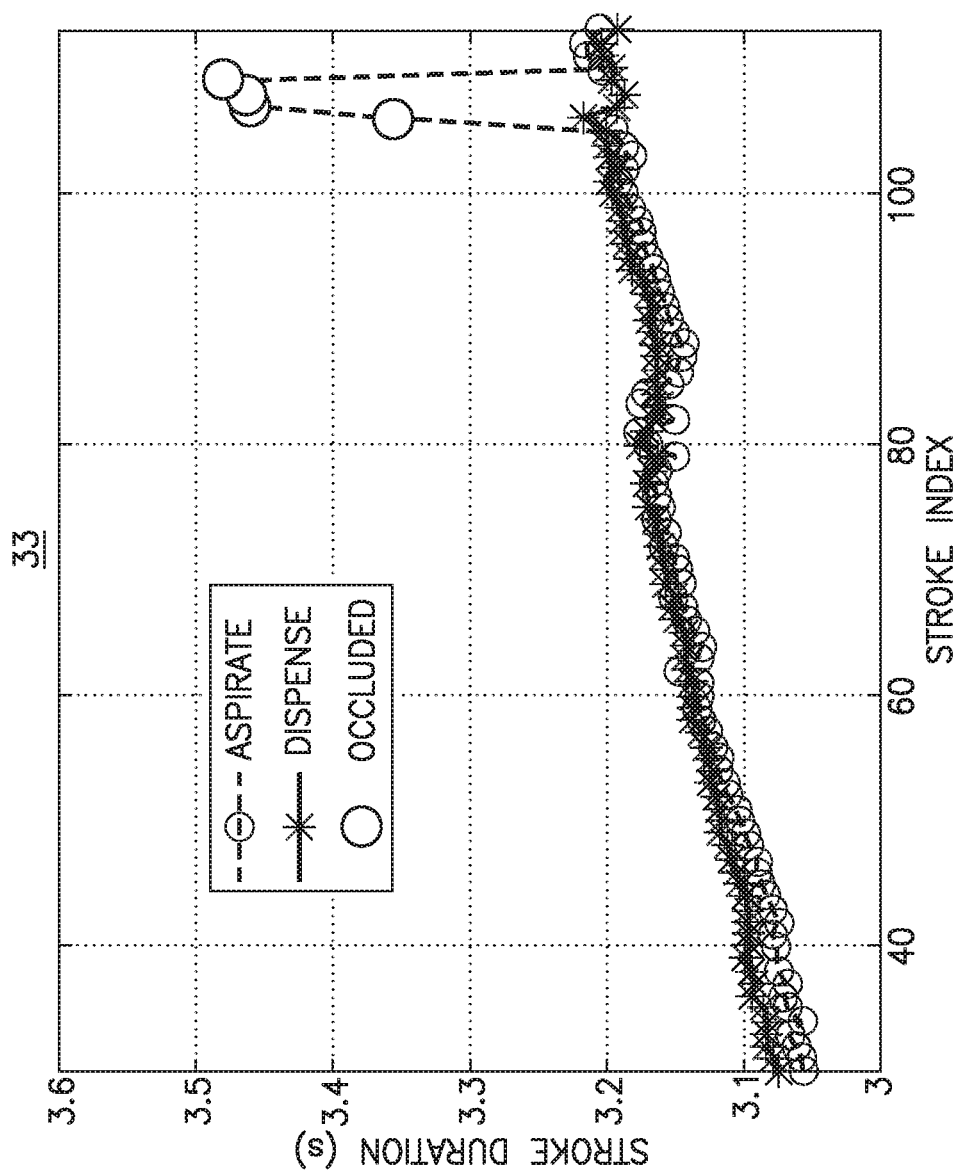
Figure 12D:
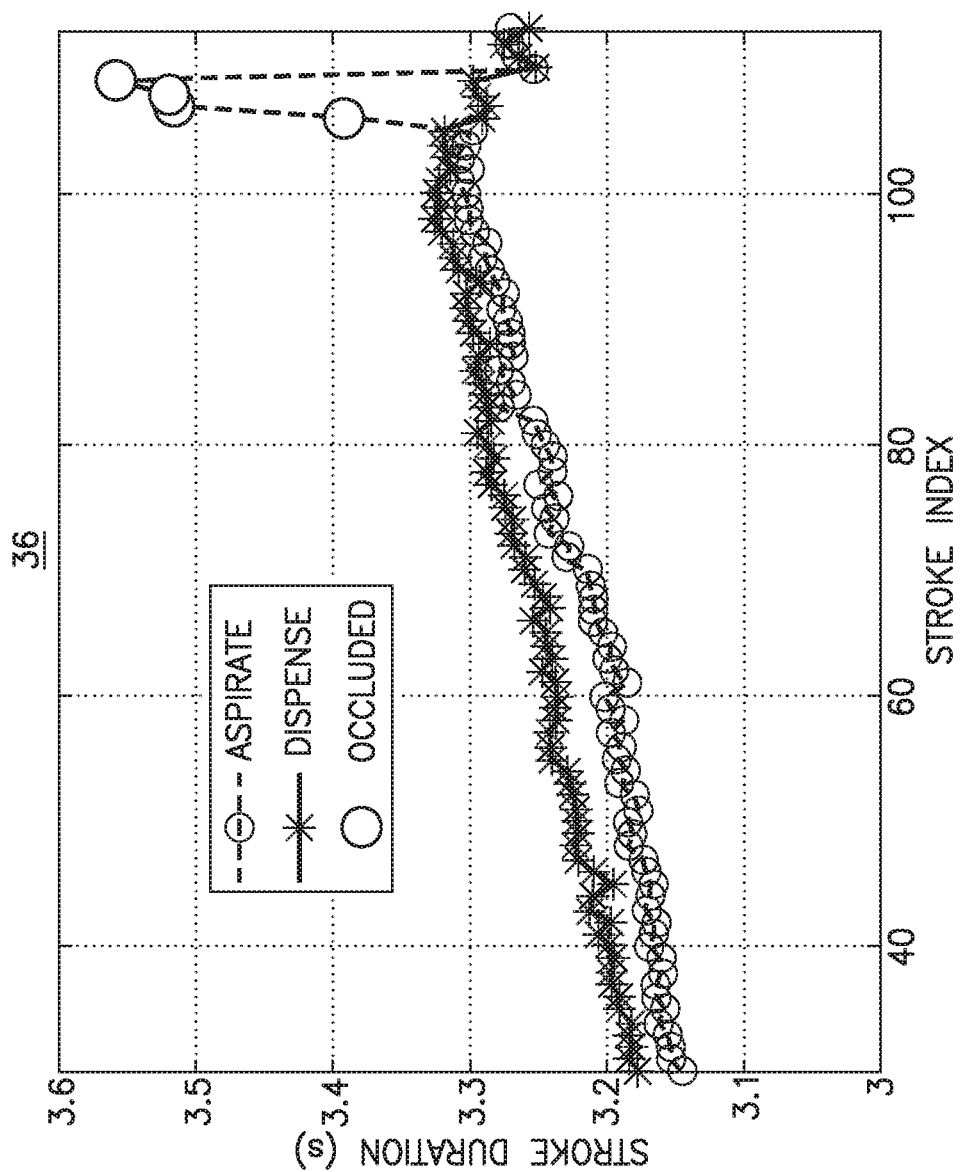
Figure 13:
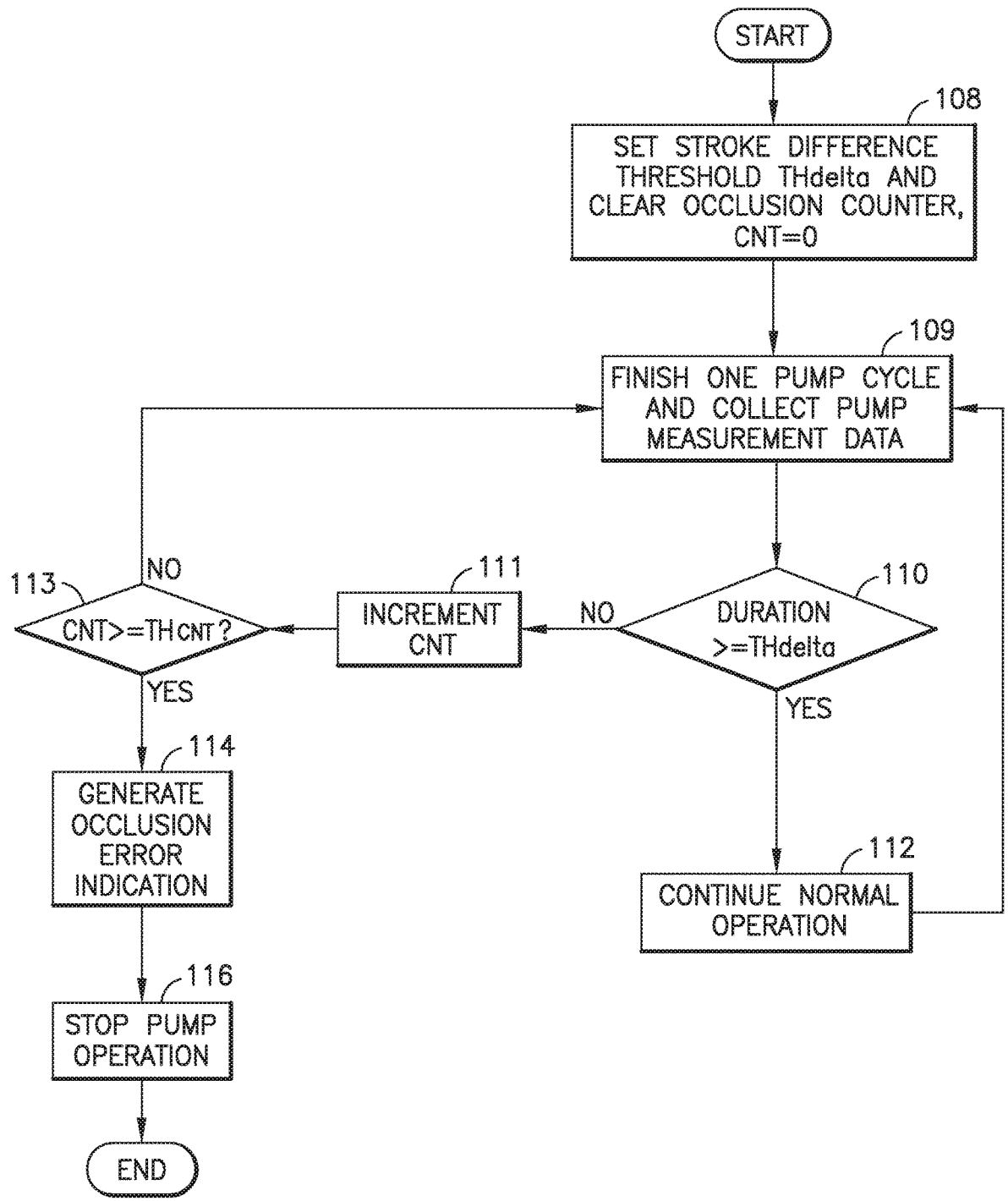
FIG. 13 is a flow chart of illustrative operations of an example medication delivery device that operates in accordance with an occlusion detection algorithm employing leak detection criteria in accordance with an illustrative embodiment of the present invention.
Figure 14:
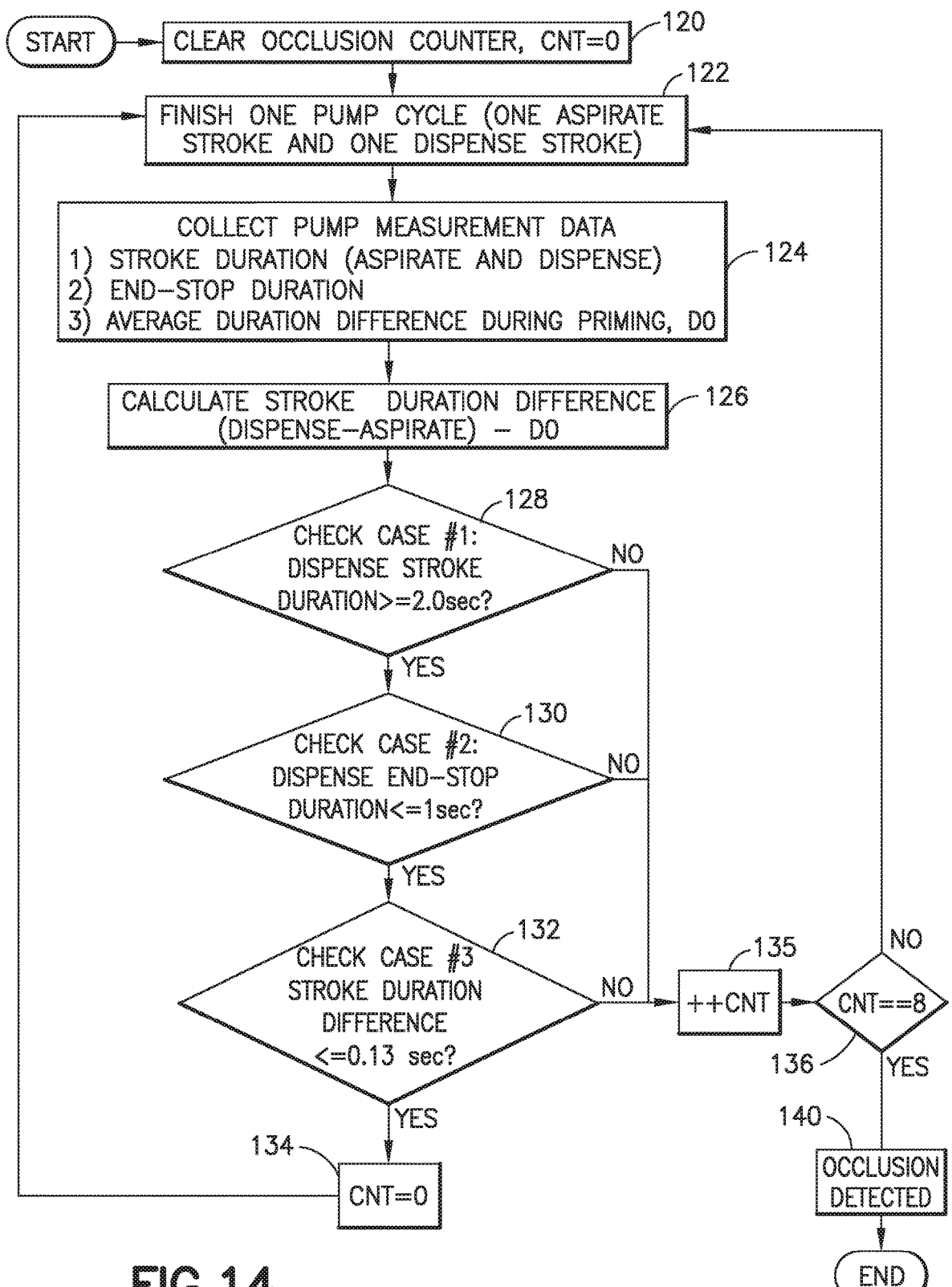
FIG. 14 is a flow chart of illustrative operations of an example medication delivery device that operates in accordance with an occlusion detection algorithm employing a combination of criteria in accordance with an illustrative embodiment of the present invention.

The occlusion detection algorithm can comprise the leak detection criteria described with FIG. 13, in combination with the stroke duration criteria described with FIG. 7 and/or the end-stop or limit switch activation duration criteria described with FIG. 9 in accordance with other illustrative embodiments. For example, detection using all three of the criteria or only a single criterion or subset of these three criteria can be implemented in parallel or in series using occlusion detection software provided to the microcontroller 58 or to the controller of a separate device associated with the medication delivery device 10. Additional example data for the stroke duration criteria is shown in FIG. 10, and additional example data for the switch activation duration criteria is shown in FIG. 11. With reference to FIG. 14, an example occlusion detection algorithm in accordance with an illustrative embodiment employs a combination of stroke duration criteria as described with FIG. 7, end-stop or limit switch activation duration criteria as described with FIG. 9, and leak detection criteria as described with FIG. 13. A counter for detected occlusion conditions is cleared or set to a 0 value (block 120). A pump cycle is detected (i.e., an aspirate stroke and a dispense stroke are detected using, for example, end-stop switch activation data) as indicated at block 122. Pump measurement data is collected (block 124) such as stroke duration, end-stop duration as described with reference to FIG. 9, and average duration difference between the aspirate stroke and the dispense stroke during priming. The stroke duration difference is determined (i.e., subtracting the average duration difference during priming from the duration corresponding to the dispense stroke duration less the aspirate stroke duration (block 126). The counter is incremented (block 136) if abnormal pump operating conditions are detected such as dispense stroke duration shortening (e.g., less than a $Th_{stroke}$ of 2 seconds) per block 128, or end-stop switch activation duration lengthening (e.g., greater than a $Th_{switch}$ of 1 second) per block 132, or a stroke duration difference (e.g., a difference of greater than $Th_{delta}$ of 0.13 microseconds) per block 134. When the counter reaches a selected value (e.g., the counter value of 8 corresponding to 8 pump cycles wherein a threshold for normal operation is not met) per block 138, then occlusion is detected per block 140 and an occlusion indication can be generated and/or pump operation can be terminated, for example. If none of these occlusion conditions are met, the counter remains cleared (e.g., 0 value) per block 134, and the next pump cycle is detected and related pump timing or measurement data is collected per block 122.

For example, the leak detection criteria described with the occlusion detection algorithm in connection with FIG. 13 above was applied to the bench occlusion data collected from 280 medication delivery devices 10 in combination with the short stroke duration algorithm (e.g., described above with reference to blocks 80 and 82 in FIG. 7) and the long end-stop duration algorithm (e.g., described above with reference to blocks 96 and 98 in FIG. 9). Table 1 shows the comparison between without and with the leak detection algorithm described with reference to blocks 108 and 110 in FIG. 13. It can be seen that the leak detection algorithm (e.g., blocks 108 and 110 in FIG. 13) significantly improved the correct detection rate of occlusion by the occlusion detection algorithm in accordance with illustrative embodiments of the present invention. However, it increases the false positive rate slightly.

TABLE 1

Occlusion Detection w/ and w/o Leak Detection

| | Total # Samples | # Detected | # False Negative (Miss) | # False Positive (False Alarm) | Correct Detection Rate |
|---|---|---|---|---|---|
| w/o Leak Detection | 280 | 89 | 181 | 0 | 32% |
| w/ Leak Detection | 280 | 270 | 5 | 5 | 96% |

Out of the 280 medication delivery devices 10, there were 120 medication delivery devices 10 that delivered a 10 U bolus before clamping. The manifold seals 49 in these medication delivery devices 10 were minimally used. Table 2 shows the comparison between without and with the leak detection algorithm for this medication delivery devices 10 group. It can be seen from Table 2 that if the manifold seals 49 are minimally used, the occlusion detection rate is quite high, 88%, even without the leak detection algorithm added to the occlusion detection algorithm employing analysis of stroke duration measurements and/or long end-stop duration pump measurements. These results are consistent with the fact that the leak is mostly caused by the wear and tear of the manifold seal after repetitive pumping motions.

TABLE 2

Occlusion Detection with and without Leak Detection for a subgroup of medication delivery devices 10 (10 U bolus before clamping)

| | Total # Samples | # Detected | # False Negative (Miss) | # False Positive (False Alarm) | Correct Detection Rate |
|---|---|---|---|---|---|
| w/o Leak Detection | 120 | 106 | 14 | 0 | 88% |
| w/ Leak Detection | 120 | 120 | 0 | 0 | 100% |

Accordingly, a leak detection criteria can be implemented in the occlusion detection algorithm. Since this algorithm only needs pump duration information to analyze leak detection criteria, there is no hardware change required. The occlusion detection algorithm employing leak detection criteria is improved when implemented in tandem with the stroke duration criteria and/or the end-stop switch activation duration criteria in order to more fully capture all significant pump behaviors during an occlusion.

In accordance with yet another illustrative embodiment, pump motor current is used to detect occlusion. Under the normal working condition, the medication delivery device 10 aspirates from the reservoir 70, which is at the upstream of the fluid path, and dispenses to patient body, which is at the end of the downstream fluid path. During the aspirate stroke, the piston opens the pump chamber, which allows the fluid from the reservoir to fill the chamber. During the dispense stroke, the piston closes the pump chamber, which pushes the fluid to the downstream. FIGS. 3A and 3B depict an example piston and the pump chamber.

When the medication delivery device 10 is occluded, the piston cannot empty the fluid inside the pump chamber to the downstream. As a result, the pump may 1) hold the fluid inside the pump chamber, 2) pump the fluid back to the reservoir, or 3) the fluid may be forced to leak through the manifold seal of the pump. Since it takes more energy to pump the fluid to any of these three pathways, the motor current is higher during the dispense stroke when occlusion happens. Therefore, motor current can be used to detect occlusion.

Figure 15:
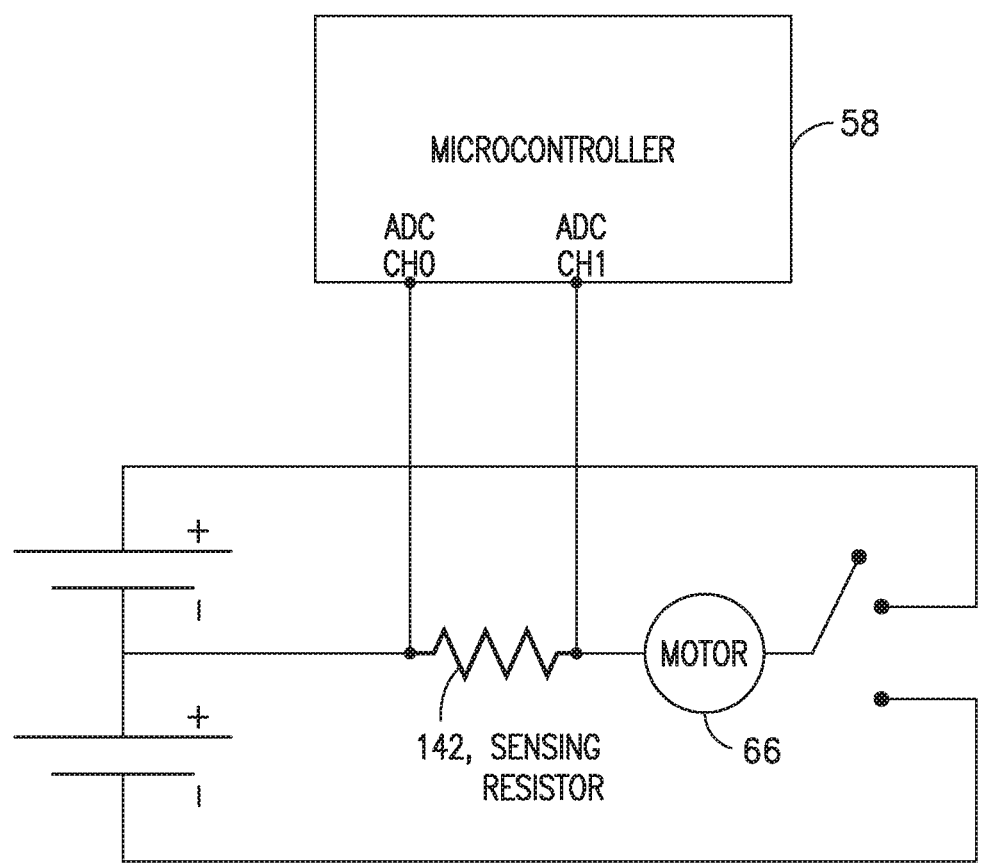
FIG. 15 is a schematic diagram of a medication delivery device pump motor having a current sensor in accordance with an illustrative embodiment of the present invention.

FIG. 15 shows an example apparatus for motor current sensing. A sensing resistor 142 is added to the PCB 92 to enable motor current measurement. The voltage drop on the sensing resistor 142 is provided into the analog-to-digital converter (ADC) of the microcontroller 58. The occlusion condition is then calculated by the microcontroller 58, and an occlusion event is reported by the microcontroller 58 when, for example, a designated occlusion signature is detected. Other components can be used for current sensing to facilitate pump motor current measurement. For example, for a pulse width modulation (PWM) drive motor used as a pump actuator 66, motor current information can be extrapolated from PWM data.

An illustrative occlusion detection algorithm for each pump cycle is described below with reference to FIG. 16. A counter for detected occlusion conditions is cleared or set to a 0 value (block 150). Motor current is determined during an aspirate stroke of a pump cycle (block 152) For example, at the start of an aspirate stroke, motor current is recorded via the microcontroller 58 during the aspirate stroke. Using $x_{in}(t)$, where t is the time referencing to the beginning of this stroke, at the conclusion of the aspirate stroke (e.g., when an end-stop signal is detected), the microcontroller 58 can be programmed to determine average motor current $A_{in}$ between 1 seconds (sec) and 2.5 sec relative to the start of the motor current as follows:

$$A_{in} = \mathrm{mean}[x_{in}(t), 1 \text{ sec} < t < 2.5 \text{ sec}].$$

It is to be understood that other methods of determining motor current during a pump cycle or aspirate or dispense stroke can be used.

Motor current is also determined during a dispense stroke of a pump cycle (block 154) For example, at the start of a dispense stroke, the microcontroller 58 records motor current during the dispense stroke. Using $x_{out}(t)$, where t is the time referencing to the beginning of this stroke, at the conclusion of the dispense stroke (e.g., when a corresponding end-stop signal is detected), the microcontroller 58 can be programmed to determine average motor current $A_{out}$ between 1 sec and 2.5 sec relative to the start of the motor current, as follows:

$$A_{out}=\text{mean}[x_{out}(t), 1 \text{ sec} < t < 2.5 \text{ sec}].$$

Figure 16:
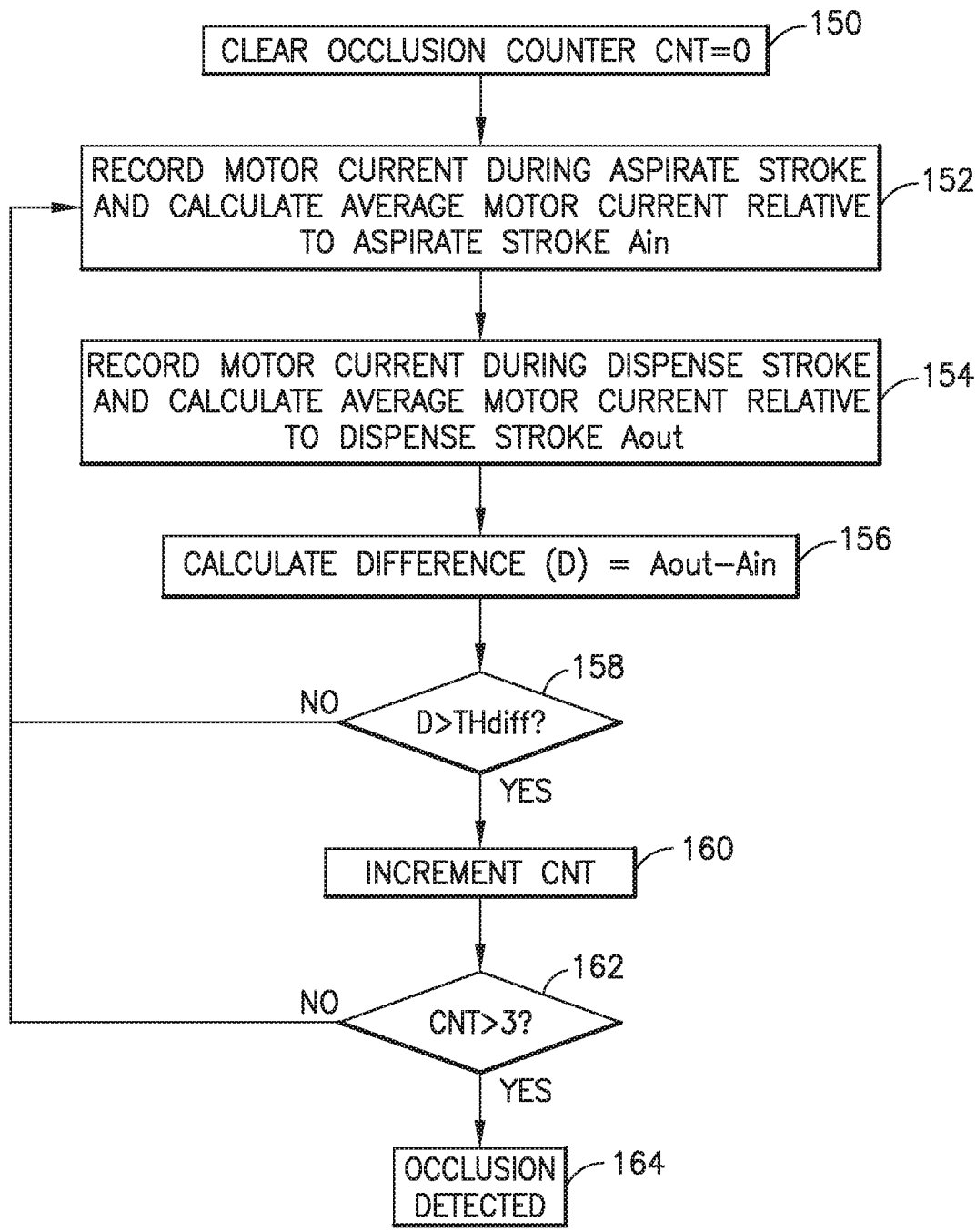
FIG. 16 is a flow chart of illustrative operations of an example medication delivery device that operates in accordance with an occlusion detection algorithm employing pump motor current criteria in accordance with an illustrative embodiment of the present invention.
Figure 17A:
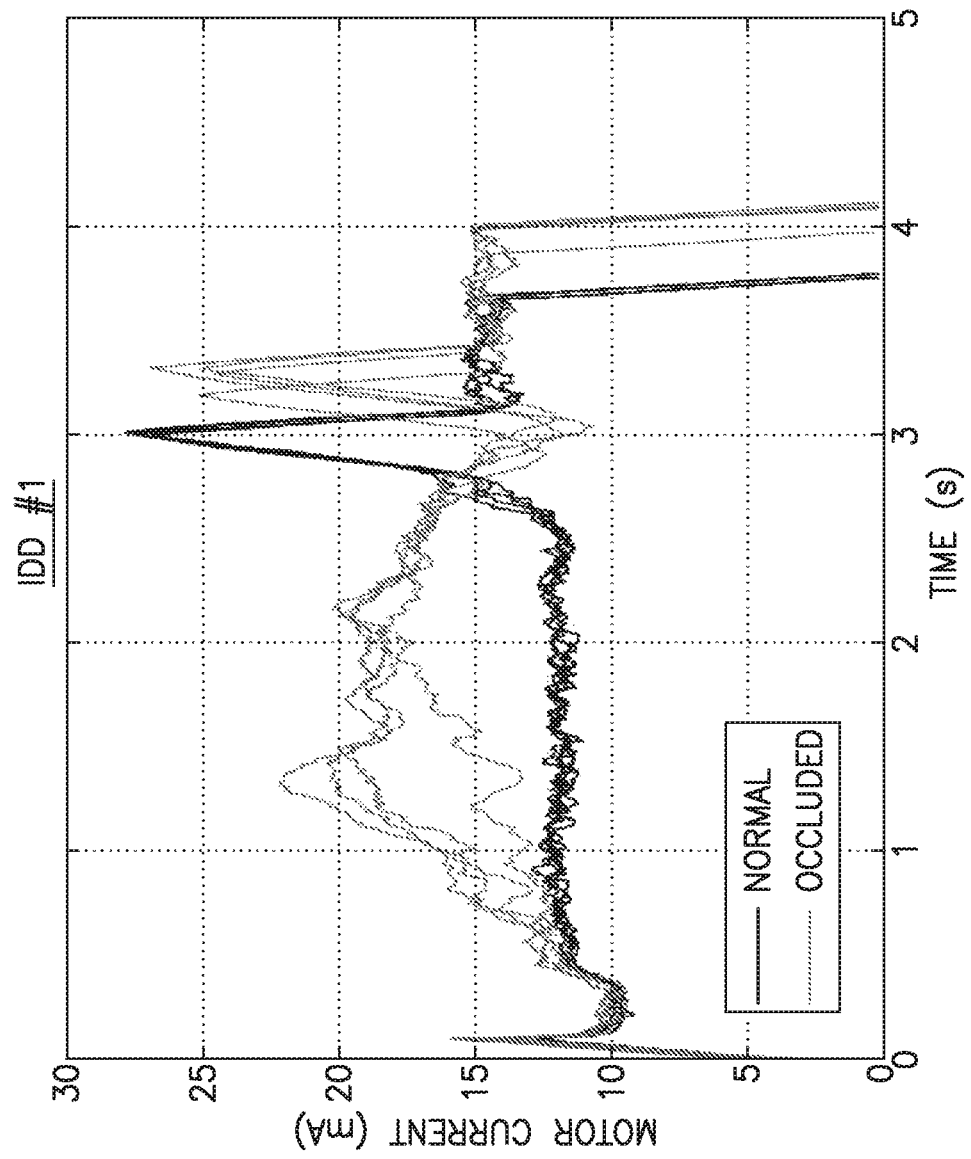
FIGS. 17A, 17B, 17C, 17D and 17E depict pump measurement data from respective example delivery devices indicating motor current during a dispense stroke before and after occlusion.
Figure 17B:
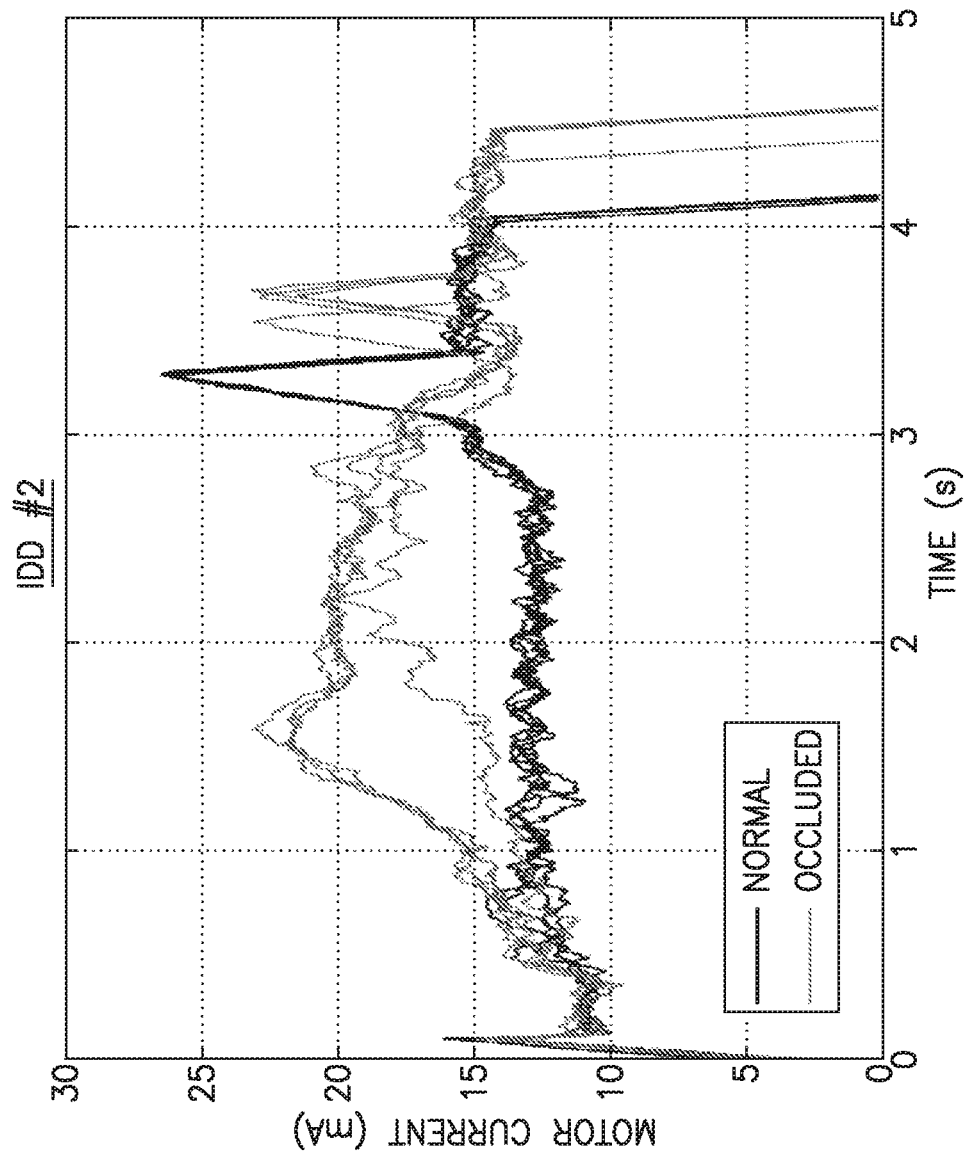
Figure 17C:
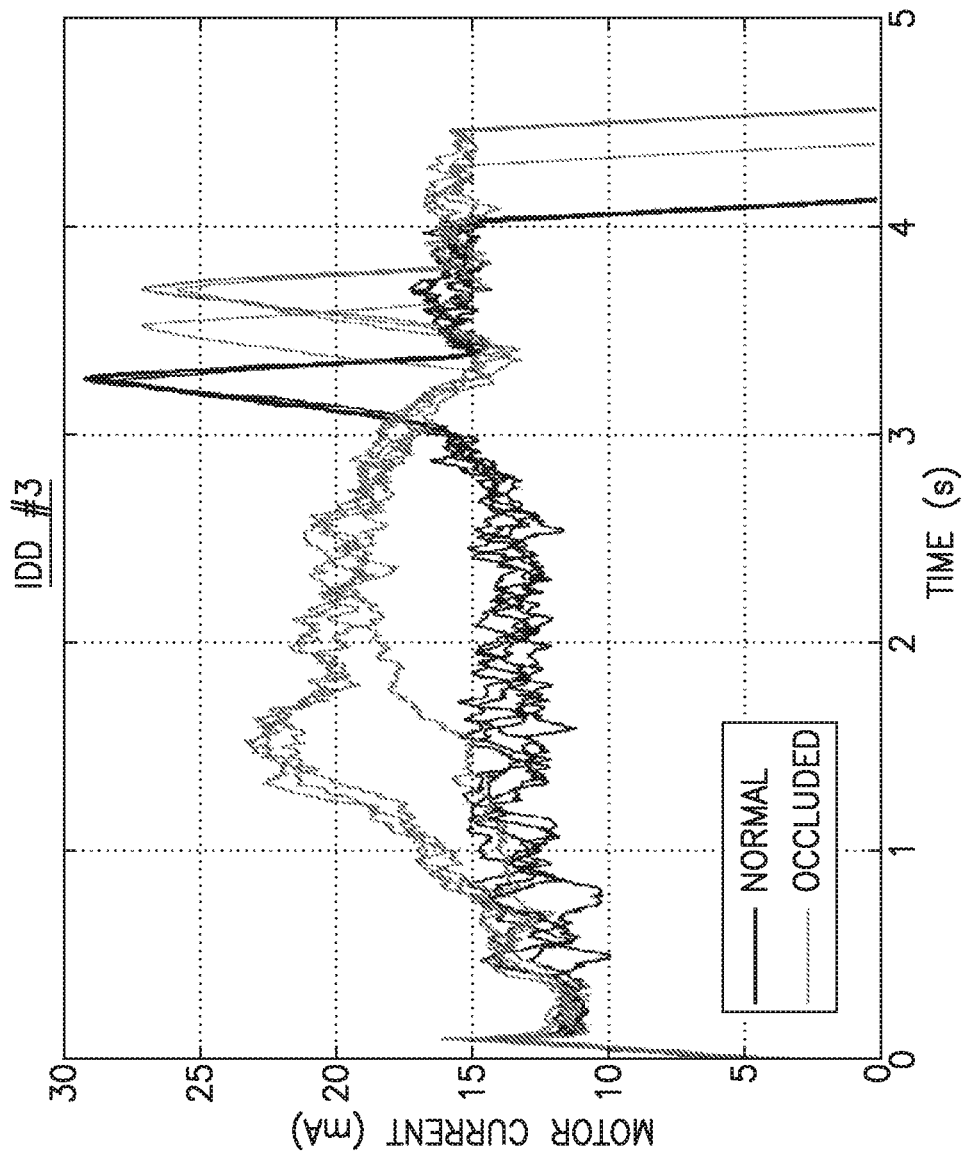
Figure 17D:
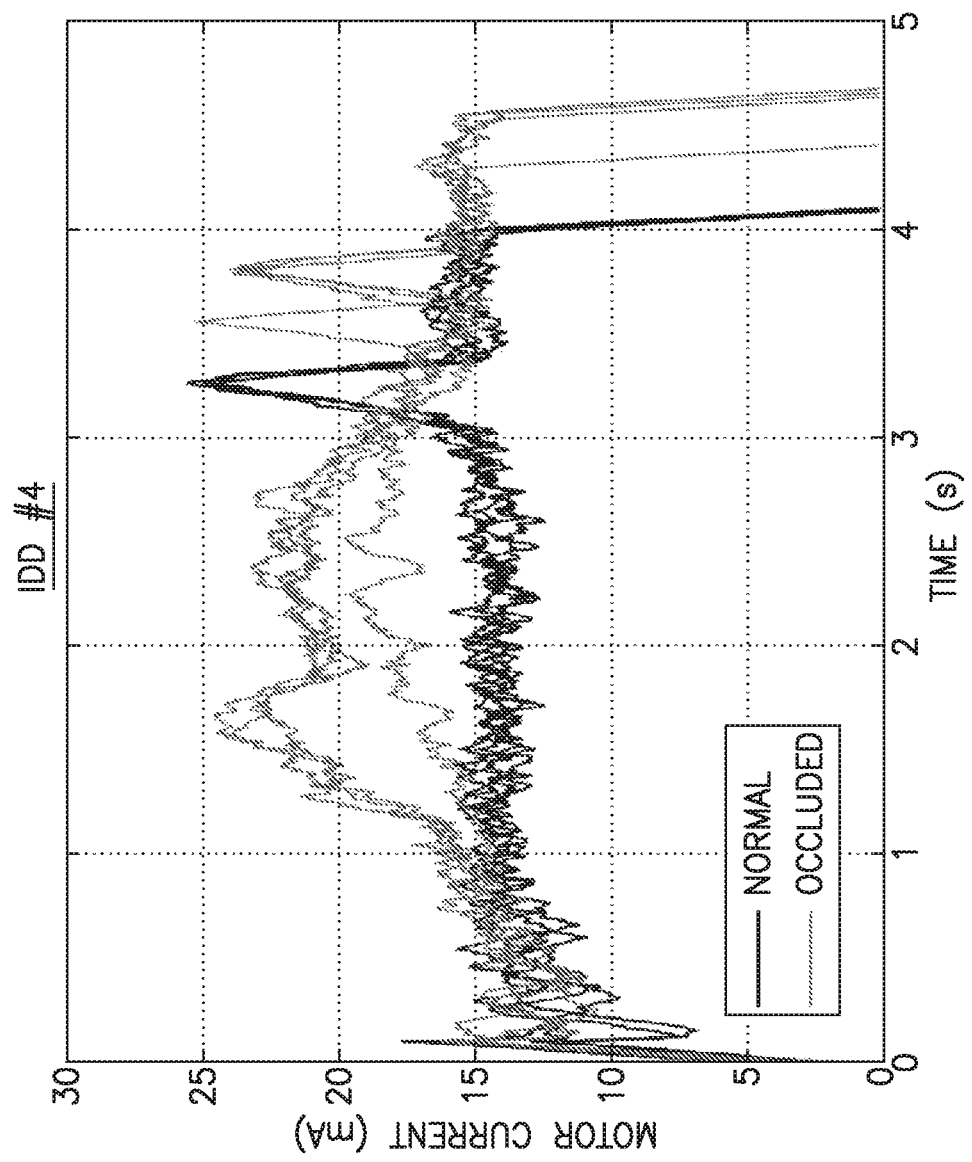
Figure 17E:
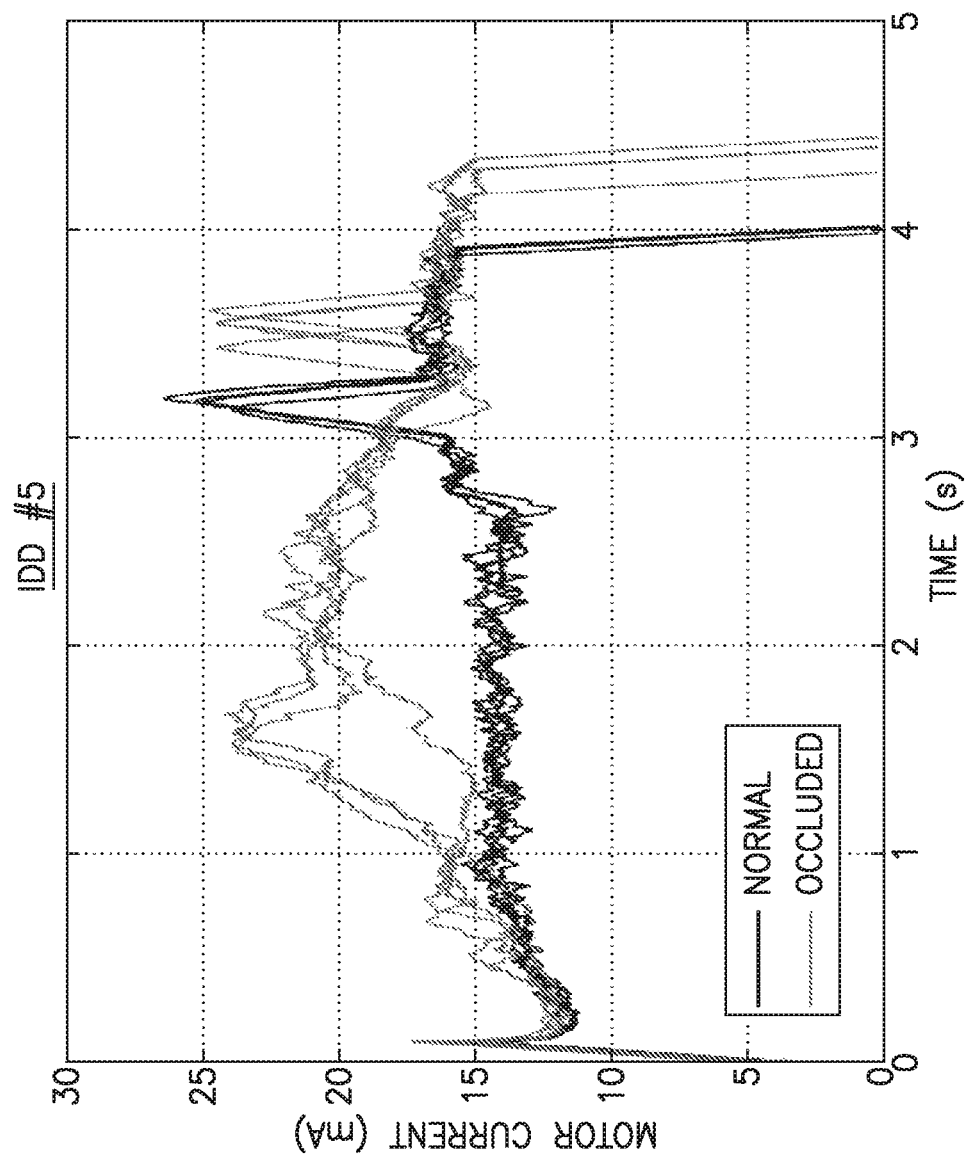
Figure 18B:
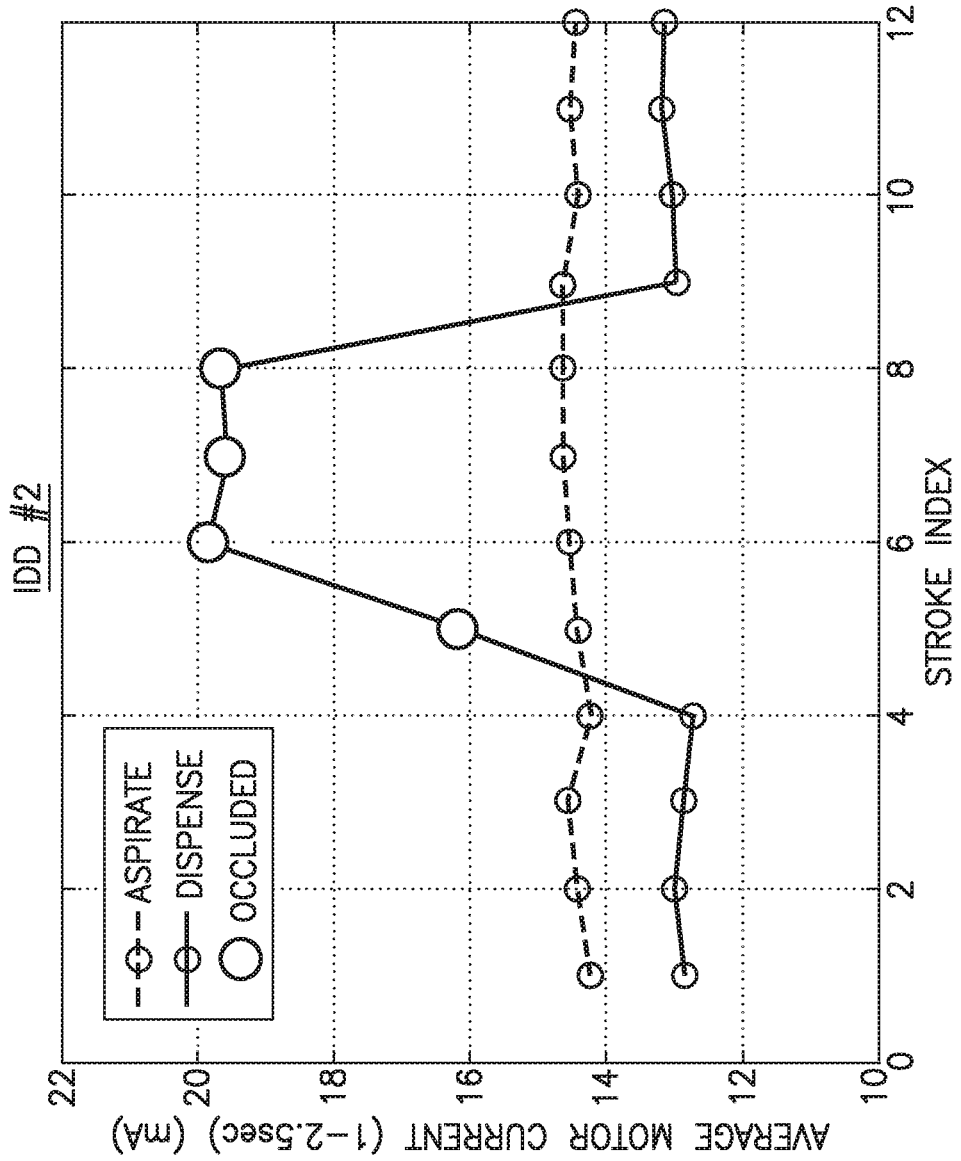
Figure 18C:
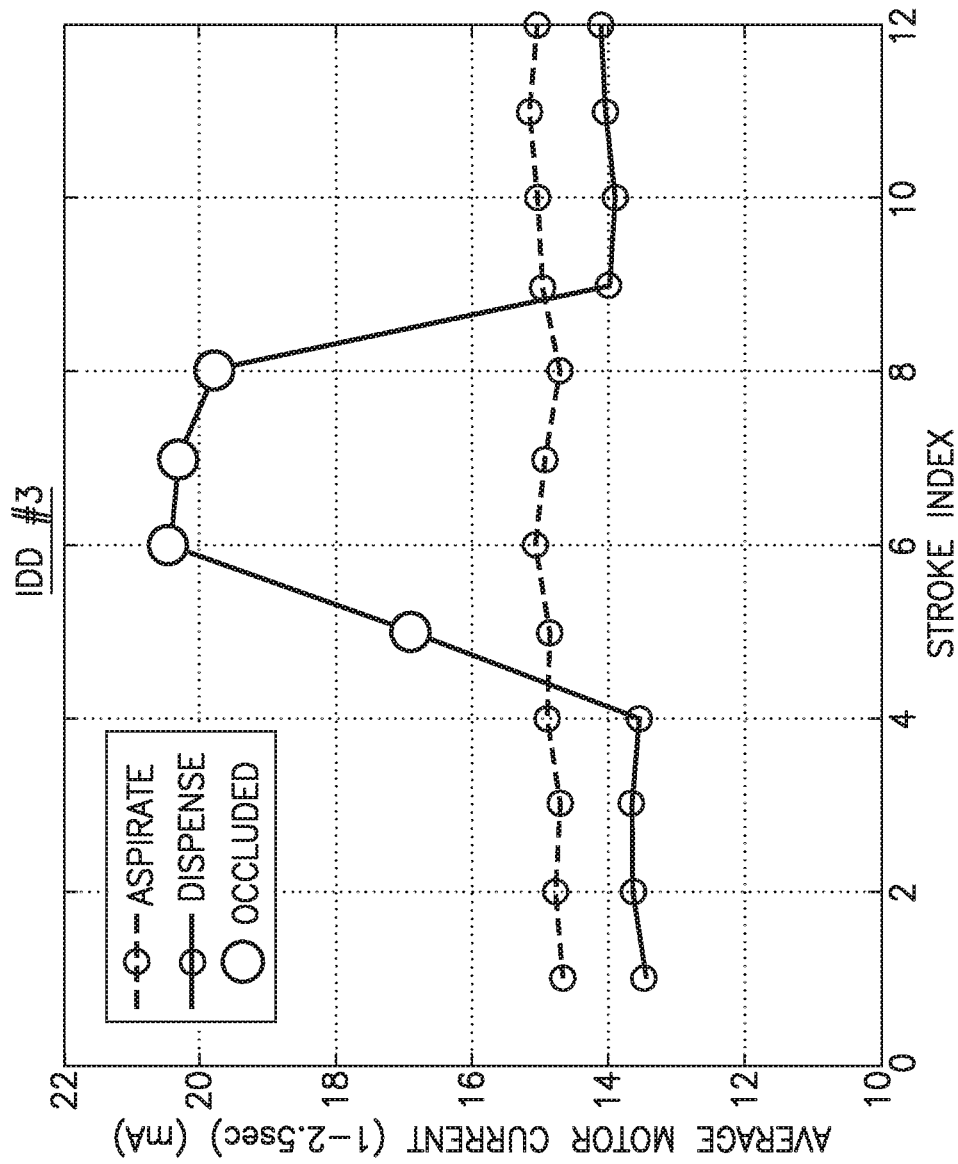
Figure 18D:
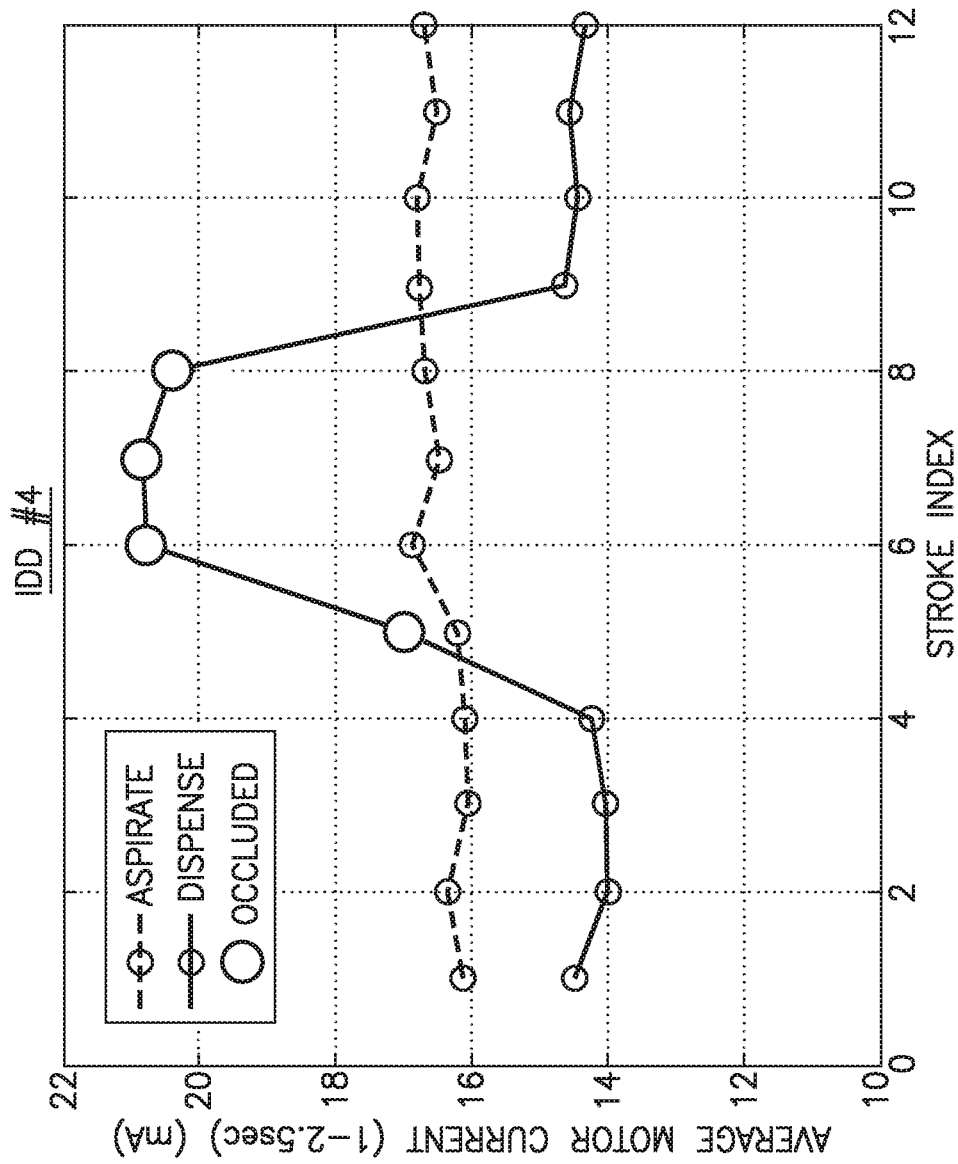
Figure 18E:
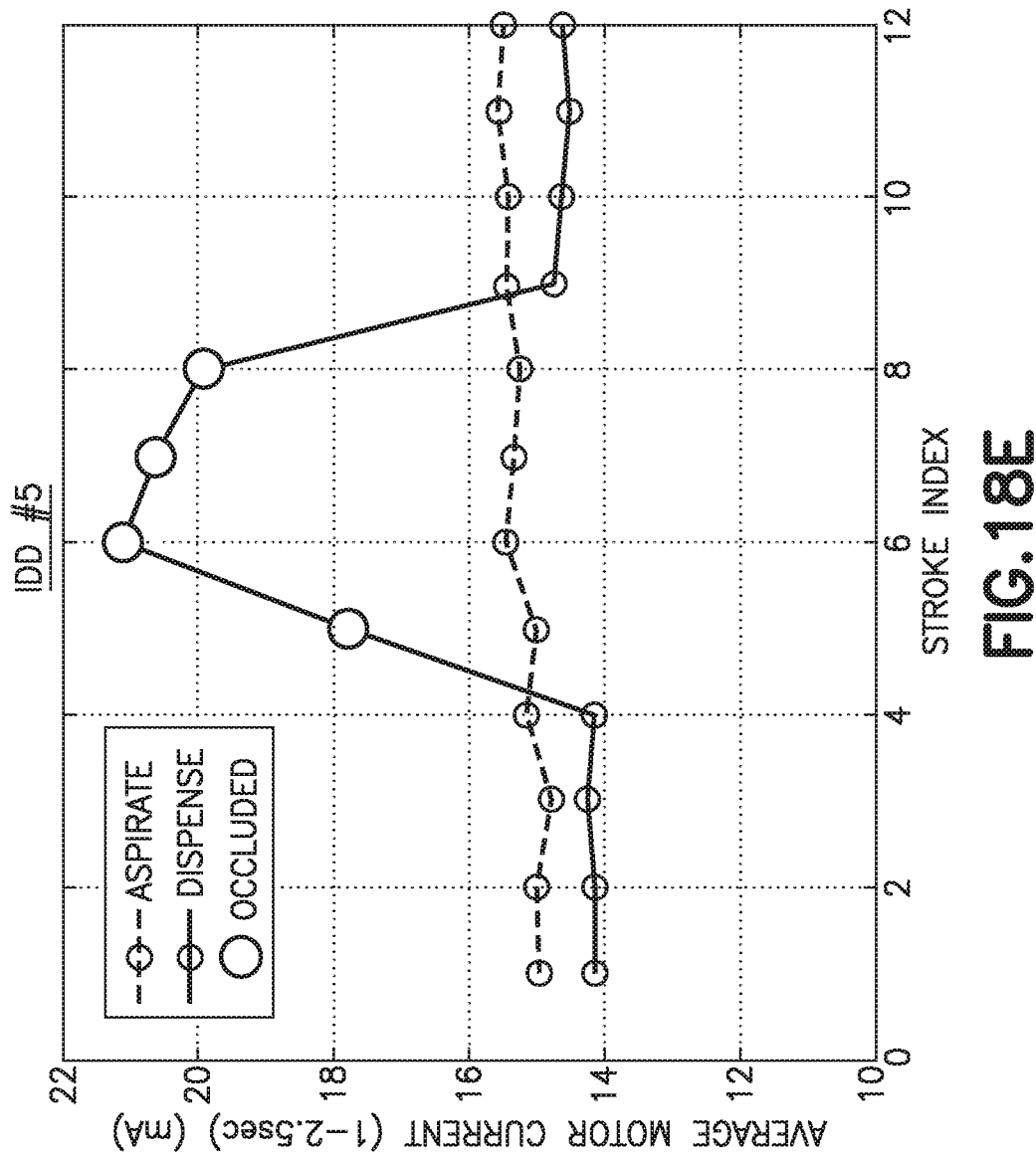

With reference to block 156 of FIG. 16, the microcontroller 58 is configured to calculate the motor current difference (D) between the aspirate stroke and the dispense stroke denote as D, where $$D=A_{out}-A_{in}.$$

If the difference (D) is larger than a designated threshold $\text{Th}_{iDiff}$ (block 158), a counter is incremented (block 160). With reference to block 162, when the counter reaches a selected value (e.g., the counter value of 3 corresponding to 3 pump cycles wherein a threshold $\text{Th}_{iDiff}$ for normal operation is not met), then occlusion is detected and an occlusion indication can be generated per block 164 and pump operation can be terminated. It is to be understood that the counter value can be another value than 3 for designating a different number of cycles over which the pump current exceeds a threshold before occlusion is indicated as detected. If the counter, after being incremented per block 160, has not yet reached the selected counter value (block 162), then the pump measurement data (e.g., motor current) continues to be collected per block 152. Thus, if the latest pump cycle and a few consecutive previous pump cycles have D values larger than a given threshold, occlusion is indicated; otherwise, normal operation of the pump is continued.

FIGS. 17A through 17E each show motor current during a dispense stroke before and after occlusion measured from five respective example delivery devices 10. FIGS. 17A through 17E depict a clear distinction of motor current between the normal and the occluded pump strokes, which facilitates use of an occlusion detection algorithm based on motor current such as the algorithm described above in connection with FIG. 16.

FIGS. 18A through 18E each show the average motor current from 1 second to 2.5 seconds (i.e., measured over a duration of 1-2.5 seconds after a stroke commences where t=0 is the start of the stroke). Again, there is clear distinction between occluded strokes and normal strokes illustrated in FIGS. 18A through 18E. Accordingly, occlusion can be detected by applying a threshold $\text{Th}_{iDiff}$ to the averaged motor current.

With continued reference to FIG. 16, FIGS. 17A through 17E, and FIGS. 18A through 18E, an alternative approach can be to only rely on average motor current for the dispense stroke and not also the aspirate stroke, in which case calculation of average motor current for aspirate strokes and D=Aout−Ain would not be needed. For example, such an alternative algorithm can comprise the following operations: motor current is determined during a dispense stroke of a pump cycle. For example, at the start of a dispense stroke, the microcontroller 58 records motor current during the dispense stroke. Using $x_{out}(t)$, where t is the time referencing to the beginning of this stroke, at the conclusion of the dispense stroke (e.g., when a corresponding end-stop signal is detected), the microcontroller 58 can be programmed to determine average motor current $A_{out}$ between 1 sec and 2.5 sec relative to the start of the motor current, as described above in connection with FIG. 16. If the average motor current $A_{out}$ is larger than a designated threshold $\text{Th}_{Aout}$, a counter is incremented. When the counter reaches a selected value (e.g., the counter value of 3 corresponding to 3 pump cycles wherein the threshold $\text{Th}_{Aout}$ for normal operation is not met), then occlusion is detected and an occlusion indication can be generated and pump operation can be terminated. It is to be understood that the counter value can be another value than 3 for designating a different number of cycles over which the pump current exceeds a threshold before occlusion is indicated as detected. If the counter, after being incremented, has not yet reached the selected counter value, then the pump measurement data (e.g., motor current) continues to be collected. Using motor current data from both the aspirate stroke and the dispense stroke as described above with FIG. 16; however, is likely to be more robust in terms of sensitivity and accuracy of occlusion detection using motor current, for example.

With reference to FIG. 19, the occlusion detection algorithm can comprise the motor current criteria described with FIG. 16, in combination other criteria used to detect an occlusion. For example, an example occlusion detection algorithm in accordance with an illustrative embodiment in FIG. 19 employs a combination of motor current criteria described with FIG. 16 with stroke duration criteria as described with FIG. 7, end-stop or limit switch activation duration criteria as described with FIG. 9, and leak detection criteria as described with FIG. 13. A counter for detected occlusion conditions is cleared or set to a 0 value (block 170). A pump cycle is detected (i.e., an aspirate stroke and a dispense stroke are detected using, for example, end-stop switch activation data) as indicated at block 172. Pump measurement data is collected (block 174) such as stroke duration, end-stop duration as described with reference to FIG. 9, and average duration difference between the aspirate stroke and the dispense stroke during priming, and average motor current during each of the aspirate stroke and the dispense stroke, for example. The stroke duration difference is determined (i.e., subtracting the average duration difference during priming from the duration corresponding to the dispense stroke duration less the aspirate stroke duration (block 176). The difference (D) in the average motor current for the dispense stroke as compared with the aspirate stroke is also calculated (block 178). The counter is incremented (block 192) if abnormal pump operating conditions are detected such as dispense stroke duration shortening (e.g., less than a $\text{Th}_{stroke}$ of 2 seconds) per block 180, or end-stop switch activation duration lengthening (e.g., greater than a $\text{Th}_{switch}$ of 1 second) per block 182, or a stroke duration difference (e.g., a difference of greater than $\text{Th}_{delta}$ of 0.13 microseconds) per block 184, or a difference in average motor current as between dispense and aspirate strokes that is larger than a designated threshold $\text{Th}_{iDiff}$ per block 186. When the counter reaches a selected value (e.g., the counter value of 8 corresponding to 8 pump cycles wherein a threshold for normal operation is not met) per block 194, then occlusion is detected per block 196 and an occlusion indication can be generated and/or pump operation can be terminated, for example. If none of these occlusion conditions are met, the counter remains cleared (e.g., 0 value) per block 190, and the next pump cycle is detected and related pump timing or measurement data is collected per block 172. It is to be understood that one or more of the blocks 180, 182, 184 and 186 and their corresponding pump measurement data collection or calculation can be omitted to achieve an alternative illustrative algorithm that employs the remaining ones of the blocks 180, 182, 184 and 186 It will be understood by one skilled in the art that this disclosure is not limited in its application to the details of construction and the arrangement of components set forth in the following description or illustrated in the drawings.

The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The components of the illustrative devices, systems and methods employed in accordance with the illustrated embodiments of the present invention can be implemented, at least in part, in digital electronic circuitry, analog electronic circuitry, of in computer hardware, firmware, software, or in combinations of them. These components can be implemented, for example, as a computer program product such as a computer program, program code or computer instructions tangibly embodied in an information carrier, or in a machine-readable storage device, for execution by, or to control the operation of, data processing apparatus such as a programmable processor, a computer, or multiple computers.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network. Also, functional programs, codes, and code segments for accomplishing illustrative embodiments of the present invention can be easily construed as within the scope of the invention by programmers skilled in the art to which the present invention pertains. Method steps associated with the illustrative embodiments of the present invention can be performed by one or more programmable processors executing a computer program, code or instructions to perform functions (e.g., by operating on input data and/or generating an output). Method steps can also be performed by, and apparatus of the illustrative embodiments of the invention can be implemented as, special purpose logic circuitry, e.g., an FPGA (field programmable gate array) or an ASIC (application-specific integrated circuit), for example.

The various illustrative logical blocks, modules, and circuits described in connection with the embodiments disclosed herein may be implemented or performed with a general purpose processor, a digital signal processor (DSP), an ASIC, a FPGA or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example, semiconductor memory devices, e.g., electrically programmable read-only memory or ROM (EPROM), electrically erasable programmable ROM (EEPROM), flash memory devices, and data storage disks (e.g., magnetic disks, internal hard disks, or removable disks, magneto-optical disks, and CD-ROM and DVD-ROM disks). The processor and the memory can be supplemented by, or incorporated in special purpose logic circuitry.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention. A software module may reside in random access memory (RAM), flash memory, ROM, EPROM, EEPROM, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. In other words, the processor and the storage medium may reside in an integrated circuit or be implemented as discrete components.

Computer-readable non-transitory media includes all types of computer readable media, including magnetic storage media, optical storage media, flash media and solid state storage media. It should be understood that software can be installed in and sold with a central processing unit (CPU) device. Alternatively, the software can be obtained and loaded into the CPU device, including obtaining the software through physical medium or distribution system, including, for example, from a server owned by the software creator or from a server not owned but used by the software creator. The software can be stored on a server for distribution over the Internet, for example.

The above-presented description and figures are intended by way of example only and are not intended to limit the present invention in any way except as set forth in the following claims. It is particularly noted that persons skilled in the art can readily combine the various technical aspects of the various elements of the various illustrative embodiments that have been described above in numerous other ways, all of which are considered to be within the scope of the invention.

The invention claimed is:

1. An infusion device with integral occlusion sensing comprising:
   a pump comprising a chamber configured with at least one port to receive fluid into the chamber from a reservoir and through which the fluid flows out of the chamber, and a pumping mechanism configured to operate for a plurality of pump cycles wherein each pump cycle among the plurality of pump cycles comprises an aspirate stroke and a dispense stroke, and to control aspiration of a volume of the fluid into the chamber during the aspirate stroke of each pump cycle among the plurality of pump cycles and to control dispensing of a volume of the fluid from the chamber during the dispense stroke of each pump cycle among the plurality of pump cycles;
   a pump measurement device configured to generate pump measurements related to a respective stroke in each pump cycle among the plurality of pump cycles, the respective stroke chosen from the aspirate stroke of each pump cycle among the plurality of pump cycles performed by the pump, and the dispense stroke of each pump cycle among the plurality of pump cycles performed by the pump;
   a processing device configured to analyze the pump measurements and determine when the pump measurements comprise a plurality of the pump measurements that satisfy a predetermined metric designated as an indication of an occlusion; and
   wherein the pump measurement device comprises a current sensing device configured to detect a pumping mechanism current during the respective stroke in each pump cycle among the plurality of pump cycles;
   wherein the pump measurements correspond to the pumping mechanism current detected during the respective stroke in each pump cycle among the plurality of pump cycles; and
   wherein the predetermined metric comprises an average pumping mechanism current among the respective strokes that exceeds a designated current value that is higher than an average value of the pumping mechanism current when no occlusion is occurring in the pump, the processing device being configured to determine the average pumping mechanism current as a mean of values of the pumping mechanism current over time.

2. The infusion device with integral occlusion sensing of claim 1, further comprising an indicator, the processing device being configured to operate the indicator as an occlusion alert in response to a determination that the plurality of the pump measurements satisfy the predetermined metric.

3. The infusion device with integral occlusion sensing of claim 1, wherein the processing device is configured to automatically terminate operation of the pumping mechanism in response to a determination that the plurality of the pump measurements satisfy the predetermined metric.

4. The infusion device with integral occlusion sensing of claim 1, wherein the pump measurements further comprise a time duration related to at least one of the aspirate stroke and the dispense stroke in each pump cycle among the plurality of pump cycles.

5. The infusion device with integral occlusion sensing of claim 4, wherein the predetermined metric further comprises a selected time duration that is shorter than an average value of the pump measurements that comprise the time duration when no occlusion is occurring in the pump.

6. The infusion device with integral occlusion sensing of claim 1, wherein the pump measurement device comprises an end-stop switch on the pump configured to be activated when the pumping mechanism completes at least one of the aspirate stroke of each pump cycle among the plurality of pump cycles and the dispense stroke of each pump cycle among the plurality of pump cycles, the end-stop switch being connected to the processing device to determine a time duration related to each of the at least one of the aspirate stroke of each pump cycle among the plurality of pump cycles and the dispense stroke of each pump cycle among the plurality of pump cycles.

7. The infusion device with integral occlusion sensing of claim 6, wherein the pump measurements further comprise a duration of end-stop switch activation that corresponds to the time duration related to each of the at least one of the aspirate stroke of each pump cycle among the plurality of pump cycles and the dispense stroke of each pump cycle among the plurality of pump cycles, and the predetermined metric further comprises a selected time duration for the end-stop switch activation that is longer than an average value of the pump measurements that comprise the time duration related to each of the at least one of the aspirate stroke of each pump cycle among the plurality of pump cycles and the dispense stroke of each pump cycle among the plurality of pump cycles when no occlusion is occurring in the pump.

8. The infusion device with integral occlusion sensing of claim 1, wherein the processing device is configured to determine, for each of the plurality of pump cycles, an average pumping mechanism current of the aspirate stroke, an average pumping mechanism current of the dispense stroke, and a difference between the average pumping mechanism current of the dispense stroke and the average pumping mechanism current of the aspirate stroke, and the predetermined metric further comprises a designated value for the difference between the average pumping mechanism current of the dispense stroke and the average pumping mechanism current of the aspirate stroke that, when exceeded, indicates the occlusion.

9. The infusion device with integral occlusion sensing of claim 8,
   wherein the pump measurement device comprises an end-stop switch on the pump configured to be activated when the pumping mechanism completes at least one of the aspirate stroke of each pump cycle among the plurality of pump cycles and the dispense stroke of each pump cycle among the plurality of pump cycles, the end-stop switch being connected to the processing device to determine a time duration related to each of the at least one of the aspirate stroke of each pump cycle among the plurality of pump cycles and the dispense stroke of each pump cycle among the plurality of pump cycles, such that the pump measurements further comprise a duration of end-stop switch activation that corresponds to the time duration related to each of the at least one of the aspirate stroke of each pump cycle among the plurality of pump cycles and the dispense stroke of each pump cycle among the plurality of pump cycles, the predetermined metric further comprises a selected time duration for the end-stop switch activation that is longer than an average value of the pump measurements that comprise the time duration related to each of the at least one of the aspirate stroke of each pump cycle among the plurality of pump cycles and the dispense stroke of each pump cycle among the plurality of pump cycles when no occlusion is occurring in the pump;

wherein the pump measurements comprise at least two of: the duration of the end-stop switch activation, the time duration related to each of the at least one of the aspirate stroke of each pump cycle among the plurality of pump cycles and the dispense stroke of each pump cycle among the plurality of pump cycles, a time difference between the at least one of the aspirate stroke of each pump cycle among the plurality of pump cycles and the dispense stroke of each pump cycle among the plurality of pump cycles, and the difference between the average pumping mechanism current of the dispense stroke and the average pumping mechanism current of the aspirate stroke; and wherein the predetermined metric further comprises predetermined metrics that correspond to respective ones of the at least two of the pump measurements, the predetermined metrics comprising the selected time duration for the end-stop switch activation, a stroke duration that corresponds to a selected time duration that is shorter than an average value of the stroke duration when no occlusion is occurring in the pump, and a dispense stroke duration difference relative to an aspirate stroke duration that corresponds to a selected time duration that is greater than an average value of a stroke duration difference when no occlusion is occurring in the pump, and the difference between the average pumping mechanism current of the dispense stroke and the average pumping mechanism current of the aspirate stroke, the processing device being configured to analyze the pump measurements and determine when the pump measurements comprise the plurality of the pump measurements that satisfy a corresponding one of the predetermined metrics.

10. The infusion device with integral occlusion sensing of claim 8, wherein the pump measurements further comprise a time duration of at least one of the aspirate stroke of each pump cycle among the plurality of pump cycles and the dispense stroke of each pump cycle among the plurality of pump cycles, and the predetermined metric further comprises a stroke duration that is a selected time duration that is shorter than an average value of a stroke duration when no occlusion is occurring in the pump, and the processing device is configured to analyze the pump measurements and determine when the pump measurements comprise a plurality of the pump measurements that satisfy at least one of a corresponding predetermined metric chosen from the average pumping mechanism current among the respective strokes, the difference between the average pumping mechanism current of the dispense stroke and the average pumping mechanism current of the aspirate stroke, and the stroke duration.

11. The infusion device with integral occlusion sensing of claim 1, wherein the pump measurements further comprise a time difference between at least one of the aspirate stroke of each pump cycle among the plurality of pump cycles and the dispense stroke of each pump cycle among the plurality of pump cycles, and the predetermined metric further comprises a stroke duration difference corresponding to a time difference of a dispense stroke duration relative to an aspirate stroke duration and is a selected time duration that is greater than an average value of the stroke duration difference when no occlusion is occurring in the pump.

12. A method of occlusion sensing in an infusion pump comprising:

operating a pump comprising a chamber configured with at least one port to receive fluid into the chamber from a reservoir and through which the fluid flows out of the chamber, and a pumping mechanism configured to operate for a plurality of pump cycles wherein each pump cycle among the plurality of pump cycles comprises an aspirate stroke and a dispense stroke, and to control aspiration of a volume of the fluid into the chamber during the aspirate stroke of each pump cycle among the plurality of pump cycles and to control dispensing of a volume of the fluid from the chamber during the dispense stroke of each pump cycle among the plurality of pump cycles;

operating a pump measurement device to generate pump measurements related to a respective stroke in each pump cycle among the plurality of pump cycles, the respective stroke chosen from the aspirate stroke of each pump cycle among the plurality of pump cycles performed by the pump, and the dispense stroke of each pump cycle among the plurality of pump cycles performed by the pump;

analyzing the pump measurements to determine when the pump measurements comprise a plurality of the pump measurements that satisfy a predetermined metric designated as an indication of an occlusion; and detecting a pumping mechanism current during the respective stroke in each pump cycle among the plurality of pump cycles;

wherein the pump measurements correspond to the pumping mechanism current detected during the respective stroke in each pump cycle among the plurality of pump cycles; and wherein the predetermined metric comprises an average pumping mechanism current among the respective strokes that exceeds a designated current value that is higher than an average value of the pumping mechanism current when no occlusion is occurring in the pump, the average pumping mechanism current being a mean of values of the pumping mechanism current over time.

13. The method of occlusion sensing of claim 12, further comprising activating, via an indicator, an occlusion alert in response to a determination that the plurality of the pump measurements satisfy the predetermined metric.

14. The method of occlusion sensing of claim 12, further comprising automatically terminating operation of the pumping mechanism in response to a determination that the plurality of the pump measurements satisfy the predetermined metric.

15. The method of occlusion sensing of claim 12, further comprising operating the pump measurement device to generate the pump measurements that further comprise a time duration related to at least one of the aspirate stroke of each pump cycle among the plurality of pump cycles and the dispense stroke of each pump cycle among the plurality of pump cycles.

16. The method of occlusion sensing of claim 15, wherein the predetermined metric further comprises a selected time duration that is shorter than an average value of the pump measurements when no occlusion is occurring in the pump, and further comprising using the predetermined metric that is the selected time duration to determine when the pump measurements that further comprise the time duration related to the at least one of the aspirate stroke of each pump cycle among the plurality of pump cycles and the dispense stroke of each pump cycle among the plurality of pump cycles indicate an occlusion.

17. The method of occlusion sensing of claim 12, further comprising:
configuring the pump measurement device as an end-stop switch on the pump that is activated when the pumping mechanism completes at least one of the aspirate stroke of each pump cycle among the plurality of pump cycles and the dispense stroke of each pump cycle among the plurality of pump cycles;
connecting the end-stop switch to a processing device configured to analyze signals from the end-stop switch to determine a time duration related to each of the at least one of the aspirate stroke of each pump cycle among the plurality of pump cycles and the dispense stroke of each pump cycle among the plurality of pump cycles.

18. The method of occlusion sensing of claim 17, wherein the pump measurements further comprise a duration of end-stop switch activation that corresponds to the time duration related to each of the at least one of the aspirate stroke of each pump cycle among the plurality of pump cycles and the dispense stroke of each pump cycle among the plurality of pump cycles, and the predetermined metric further comprises a selected time duration for the end-stop switch activation that is longer than an average value of the pump measurements that comprise the time duration related to each of the at least one of the aspirate stroke of each pump cycle among the plurality of pump cycles and the dispense stroke of each pump cycle among the plurality of pump cycles when no occlusion is occurring in the pump.

19. The method of occlusion sensing of claim 12, wherein the analyzing the pump measurements comprises determining, for each of the plurality of pump cycles, an average pumping mechanism current of the aspirate stroke, an average pumping mechanism current of the dispense stroke, and a difference between the average pumping mechanism current of the dispense stroke and the average pumping mechanism current of the aspirate stroke, and the predetermined metric further comprises a designated value for the difference between the average pumping mechanism current of the dispense stroke and the average pumping mechanism current of the aspirate stroke that, when exceeded, indicates the occlusion.

20. The method of occlusion sensing of claim 19, further comprising configuring the pump measurement device as an end-stop switch on the pump that is activated when the pumping mechanism completes at least one of the aspirate stroke of each pump cycle among the plurality of pump cycles and the dispense stroke of each pump cycle among the plurality of pump cycles such that the pump measurements further comprise a duration of end-stop switch activation that corresponds to a time duration related to each of the at least one of the aspirate stroke of each pump cycle among the plurality of pump cycles and the dispense stroke of each pump cycle among the plurality of pump cycles, the predetermined metric further comprises a selected time duration for the end-stop switch activation that is longer than an average value of the pump measurements that comprise the time duration related to each of the at least one of the aspirate stroke of each pump cycle among the plurality of pump cycles and the dispense stroke of each pump cycle among the plurality of pump cycles when no occlusion is occurring in the pump;
wherein the pump measurements comprise at least two of: the duration of the end-stop switch activation, the time duration related to each of the at least one of the aspirate stroke of each pump cycle among the plurality of pump cycles and the dispense stroke of each pump cycle among the plurality of pump cycles, a time difference between the aspirate stroke and the dispense stroke, and the difference between the average pumping mechanism current of the dispense stroke and the average pumping mechanism current of the aspirate stroke; and
wherein the predetermined metric further comprises predetermined metrics that correspond to respective ones of the at least two of the pump measurements, the predetermined metrics comprising the selected time duration for the end-stop switch activation, a stroke duration that corresponds to a selected time duration that is shorter than an average value of the stroke duration when no occlusion is occurring in the pump, a dispense stroke duration difference relative to an aspirate stroke duration that corresponds to a selected time duration that is greater than an average value of a stroke duration difference when no occlusion is occurring in the pump, and the difference between the average pumping mechanism current of the dispense stroke and the average pumping mechanism current of the aspirate stroke, and the analyzing the pump measurements comprises determining when the pump measurements comprise a plurality of the pump measurements that satisfy a corresponding one of the predetermined metrics.

21. The method of occlusion sensing of claim 12, wherein the pump measurements further comprise a time difference between at least one of the aspirate stroke of each pump cycle among the plurality of pump cycles and the dispense stroke of each pump cycle among the plurality of pump cycles, and the predetermined metric further comprises a stroke duration difference corresponding to a time difference of a dispense stroke duration relative to an aspirate stroke duration and is a selected time duration that is greater than an average value of the stroke duration difference when no occlusion is occurring in the pump.

22. The method of occlusion sensing of claim 21, wherein the pump measurements further comprise a time duration of the at least one of the aspirate stroke of each pump cycle among the plurality of pump cycles and the dispense stroke of each pump cycle among the plurality of pump cycles, and the predetermined metric further comprises a stroke duration that is a selected time duration that is shorter than an average value of a stroke duration when no occlusion is occurring in the pump, and the analyzing the pump measurements comprises determining when the pump measurements comprise a plurality of the pump measurements that satisfy at least one of a corresponding predetermined metric chosen from the average pumping mechanism current among the respective strokes, a difference between an average pumping mechanism current of the dispense stroke of each pump cycle among the plurality of pump cycles and an average pumping mechanism current of the aspirate stroke of each pump cycle among the plurality of pump cycles, and the stroke duration that is the selected time duration.

* * * * *